(12) United States Patent
Chevet et al.

(10) Patent No.: US 11,525,165 B2
(45) Date of Patent: Dec. 13, 2022

(54) METHOD OF SELECTION OF AN IRE1-INHIBITOR THERAPY FOR PATIENT SUFFERING FROM CANCER

(71) Applicants: INSERM (INSTITUT NATIONAL DE LA SANTÉ ET DE LA RECHERCHE MÉDICALE), Paris (FR); UNIVERSITÉ DE RENNES 1, Rennes (FR); ENIOS APPLICATIONS PRIVATE LIMITED COMPANY, Kallithea Athens (GR)

(72) Inventors: Eric Chevet, Rennes (FR); Aristotelis Chatziioannou, Kallithea Athens (GR)

(73) Assignees: INSERM, Paris (FR); UNIVERSITÉ DE RENNES 1, Rennes (FR); ENIOS APPLICATIONS PRIVATE LIMITED COMPANY, Kallithea Athens (GR)

( * ) Notice: Subject to any disclaimer, the term of this patent is extended or adjusted under 35 U.S.C. 154(b) by 28 days.

(21) Appl. No.: 16/955,989

(22) PCT Filed: Dec. 19, 2018

(86) PCT No.: PCT/EP2018/085771
§ 371 (c)(1),
(2) Date: Jun. 19, 2020

(87) PCT Pub. No.: WO2019/121869
PCT Pub. Date: Jun. 27, 2019

(65) Prior Publication Data
US 2020/0318203 A1    Oct. 8, 2020

(30) Foreign Application Priority Data
Dec. 20, 2017 (EP) .................................. 17306855

(51) Int. Cl.
*C12Q 1/6886*  (2018.01)
(52) U.S. Cl.
CPC ..... *C12Q 1/6886* (2013.01); *C12Q 2600/106* (2013.01); *C12Q 2600/158* (2013.01)
(58) Field of Classification Search
None
See application file for complete search history.

(56) References Cited

U.S. PATENT DOCUMENTS

2009/0285832 A1    11/2009    Teh et al.
2017/0199193 A1    7/2017    Filvaroff et al.

FOREIGN PATENT DOCUMENTS

WO    2007/101224 A2    9/2007
WO    2015/178770 A1    11/2015

OTHER PUBLICATIONS

Cobb et al (Crit Care Med 2002 vol. 30 p. 2711) (Year: 2002).*
Enard et al. (Science 2002 vol. 296 p. 340) (Year: 2002).*
Affymetrix: "GeneChip Human Genome U1333 Arrays", Datasheet Affymetrix, pp. 1-8, Jan. 1, 2003.
Harrington et al: "Unfolded Protein Response in Cancer: IRE1[alpha] Inhibition by Selective Kinase Ligands Does Not Impair Tumor Cell Viability", ACS Medicinal Chemistry Letters, vol. 6, No. 1, pp. 68-72, Sep. 29, 2014.
Pluquet et al., "Posttranscriptional Regulation of PER1 Underlies the Oncogenic Function of IREalpha", Cancer Res; 73(15); 4732-43 (2013).

* cited by examiner

*Primary Examiner* — Katherine D Salmon
(74) *Attorney, Agent, or Firm* — WCF IP

(57) ABSTRACT

The present invention relates to a method of treatment and method of therapy selection for patient suffering from cancer. The inventors provide the first demonstration of a dual role of IRE1 downstream signaling in cancer. Indeed, the inventors demonstrate that the modulation of IRE1 signaling characteristics in GBM cells controls tumor aggressiveness. Furthermore, the inventors provide evidence supporting a novel concept where IRE-downstream signals play combined/integrated roles in cancer development, where XBP1s provides pro-tumoral signals, whereas RIDD of mRNA and miR17 rather elicits anti-tumoral features. Their data, obtained using established cell lines, patient tumor samples and primary GBM lines, depict a complex scenario where IRE1 signaling orchestrates distinct aspects of GBM biology. In particular, the invention relates to a method for predicting whether a subject will be eligible to a treatment with an IRE1 RNase inhibitor.

5 Claims, 3 Drawing Sheets

Figure 1:
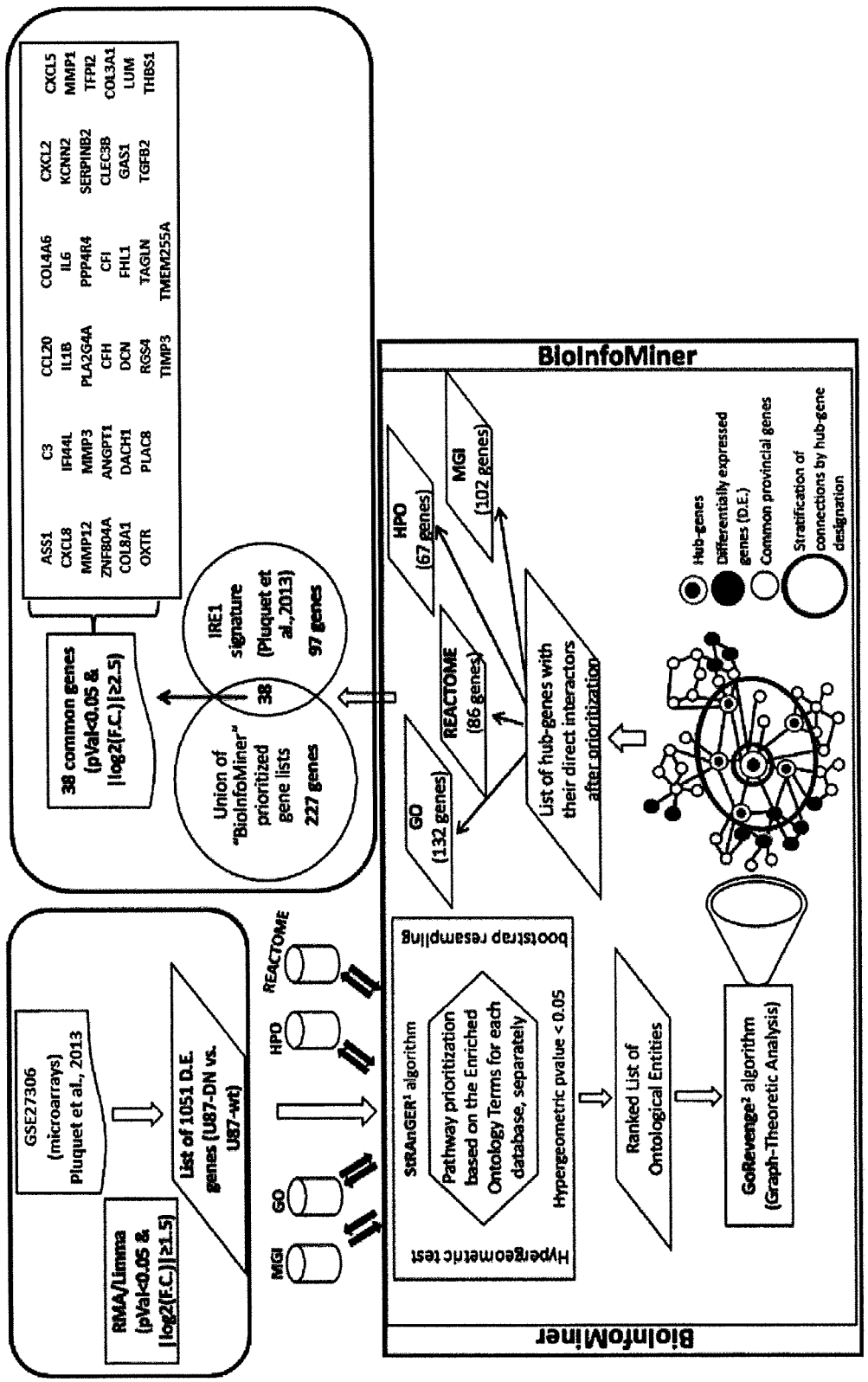

| TCGA cohort | Type of cancer | Total number of cases | n.cases by IRE1group coupled with survival data | | | | Dominant component | XBP1s/RIDD component effect on survival rates | | Type of coupled effect |
|---|---|---|---|---|---|---|---|---|---|---|
| | | | XBP1s+ /RIDD+ | XBP1s+ /RIDD- | XBP1s- /RIDD+ | XBP1s- /RIDD- | | ↑XBP1s activity | ↑RIDD activity | |
| TCGA-GBM (microarrays) | Glioblastoma multiforme | 527 | 67 | 213 | 173 | 63 | XBP1s-driven | poor prognosis | good prognosis | antagonistic effect |
| TCGA-GBM (RNAseq) | Glioblastoma multiforme | 156 | 22 | 55 | 54 | 24 | | poor prognosis | good prognosis | antagonistic effect |
| TCGA-COAD (RNAseq) | Colon Adenocarcinoma | 465 | 96 | 140 | 138 | 88 | RIDD-driven | poor prognosis | good prognosis | antagonistic effect |
| TCGA-KIRC (RNAseq) | Kidney Renal Clear Cell Carcinoma | 534 | 89 | 174 | 177 | 94 | XBP1s-driven | poor prognosis | poor prognosis | additive effect |
| TCGA-OV (RNAseq) | Ovarian Serous Cystadenocarcinoma | 373 | 61 | 125 | 124 | 62 | RIDD-driven | poor prognosis | good prognosis | antagonistic effect |
| TCGA-SKCM (RNAseq) | Skin Cutaneous Melanoma | 103 | 24 | 28 | 30 | 20 | | good prognosis | poor prognosis | antagonistic effect |
| TCGA-SKCM (microarrays) | Skin Cutaneous Melanoma | 470 | 68 | 143 | 145 | 83 | RIDD-driven | good prognosis | poor prognosis | antagonistic effect |
| TCGA-BLCA (RNAseq) | Bladder Urothelial Carcinoma | 411 | 67 | 136 | 136 | 70 | RIDD-driven | good prognosis | good prognosis | synergistic beneficial effect |
| TCGA-PAAD (RNAseq) | Pancreatic Adenocarcinoma | 177 | 37 | 53 | 56 | 31 | XBP1s-driven | poor prognosis | good prognosis | antagonistic effect |
| TCGA-BRCA (RNAseq) | Breast Invasive Carcinoma | 1086 | 199 | 361 | 355 | 168 | XBP1s-driven | good prognosis | good prognosis | synergistic beneficial effect |
| TCGA-STAD (RNAseq) | Stomach Adenocarcinoma | 375 | 99 | 107 | 92 | 73 | RIDD-driven | poor prognosis | good prognosis | antagonistic effect |
| TCGA-LIHC (RNAseq) | Liver Hepatocellular Carcinoma | 371 | 52 | 134 | 138 | 46 | XBP1s-driven | poor prognosis | poor prognosis | additive effect |
| TCGA-LUAD (RNAseq) | Lung Adenocarcinoma | 522 | 104 | 169 | 159 | 81 | RIDD-driven | poor prognosis | poor prognosis | additive effect |
| TCGA-PRAD (RNAseq) | Prostate Adenocarcinoma | 495 | | | | | no survival analysis - the majority of cases are alive | | | |
| Total | | 6065 | 985 | 1838 | 1777 | 903 | | | | |

Figure 4

METHOD OF SELECTION OF AN IRE1-INHIBITOR THERAPY FOR PATIENT SUFFERING FROM CANCER

FIELD OF THE INVENTION

The present invention relates to method of treatment and method of therapy selection for patient suffering from cancer.

BACKGROUND OF THE INVENTION

Cancer is a major concern since it is a leading cause of death worldwide, accounting for 8.2 million deaths in 2012 (world cancer report, 2014, World Health Organization). For example, cancer is the second most common cause of death in the US, exceeded only by heart diseases, and accounts for nearly 1 of every 4 deaths (cancer facts and figures 2015, American Cancer Society). Despite numerous existing treatments, it still a need for an improved method of treating cancer. Among various types of cancer, glioblastoma multiforme (GBM) is one of the most lethal adult cancers, as the majority of patients die within 15 months after diagnosis (Anton K et al (2007) Glioblastoma multiforme: overview of current treatment and future perspectives. Hematol Oncol Clin North Am 26: 825-853). GBM is an aggressive, incurable glioma (grade IV astrocytoma, WHO classification) due to great heterogeneity of cell subtypes within the tumor and to the presence of invasive spots that cannot be easily cured by surgical resection or targeted radiation. To limit tumor recurrences from invasive cells, chemotherapy (temozolomide (TMZ)) was added to surgery and radiation (Stupp R, et al (2005) Radiotherapy plus concomitant and adjuvant temozolomide for glioblastoma. The New England journal of medicine 352: 987-996). Although this combined therapy has demonstrated some efficiency, it only increases patient's median survival from 12.1 to 14.6 months. Thus, understanding biological processes of GBM progression and treatment resistance represents a major challenge to develop more effective therapies.

The ER is the major subcellular compartment involved in protein folding and secretion. Accumulating evidence support an emerging role of ER proteostasis alterations in cancer development, having been implicated in most hallmarks of cancer (Urra H, et al (2016) Endoplasmic Reticulum Stress and the Hallmarks of Cancer. Trends in Cancer 2: 252-262). ER stress triggers an adaptive reaction known as the unfolded protein response (UPR), which aims to recover proteostasis or to induce apoptosis of irreversibly damaged cells. Several studies in animal models of cancer using genetic or pharmacological manipulation of the UPR have demonstrated a functional role of this pathway in cancer (Hetz C, et al (2013) Targeting the unfolded protein response in disease. Nat Rev Drug Discov 12: 703-719). The UPR is initiated by the activation of three ER transmembrane proteins known as PERK, ATF6 and IRE1. IRE1α (referred to as IRE1 hereafter) is a serine/threonine kinase and endoribonuclease that represents the most conserved UPR signaling branch in evolution, controlling cell fate under ER stress. Once activated, IRE1 oligomerises thus engaging three major downstream outputs including the activation of JNK, the splicing of XBP1 mRNA (XBP1s) (and the degradation of targeted mRNA and miRNA, a process referred to as RNA Regulated IRE1 Dependent Decay (RIDD). Importantly, the universe of RIDD targets may depend on the tissue context and the nature of the stress stimuli, impacting different biological processes including apoptosis, cell migration and inflammatory responses (Dejeans N, et al (2014) Addicted to secrete-novel concepts and targets in cancer therapy. Trends Mol Med 20: 242-250). Several functional studies have shown that targeting the expression or the RNase activity of IRE1 reduces the progression of various forms of cancer mostly due to ablating the prosurvival effects of XBP1 on tumor growth and we have previously demonstrated its functional implication in various models of experimental glioblastoma (Jabouille A, et al (2015) Glioblastoma invasion and cooption depend on IRE1alpha endoribonuclease activity. Oncotarget 6: 24922-24934) (Pluquet O, et al (2013) Posttranscriptional regulation of PER1 underlies the oncogenic function of IREalpha. Cancer Res 73: 4732-4743). Moreover, large-scale sequencing studies on human cancer tissue samples performed by The Cancer Genome Atlas (TCGA) initiative revealed the presence of 3 somatic mutations on the IRE1 gene in GBM leading to the S769F, Q780* and P336L variants. Although a previous report aimed at understanding the structural impact of some of those mutations in IRE1 function, little is known on how their differential contribution to RIDD and XBP1 mRNA splicing impact on GBM development and progression.

SUMMARY OF THE INVENTION

The present invention relates to method of treatment and method of therapy selection for patient suffering from cancer. In particular, the present invention is defined by the claims.

DETAILED DESCRIPTION OF THE INVENTION

Here the inventors took advantage of the selective signaling properties of different IRE1 GBM somatic mutants and they demonstrate that the modulation of IRE1 signaling characteristics in GBM cells controls tumor aggressiveness, not only by providing selective advantages to the tumor cells themselves, but also by remodeling the tumor stroma to the benefit of growth. Furthermore, the inventors provide evidence supporting a novel concept where IRE-downstream signals play combined/integrated roles in cancer development, where XBP1s provides pro-tumoral signals, whereas RIDD of mRNA and miR17 rather elicits anti-tumoral features. Their data, obtained using established cell lines, patient tumor samples and primary GBM lines, depict a complex scenario where IRE1 signaling orchestrates distinct aspects of GBM biology. Thus, the inventors provide the first demonstration of a dual role of IRE1 downstream signaling in cancer and opens a new therapeutic window to abrogate tumor progression. In conclusion, they showed a new biomarkers signature that permits the identification of patient eligible—or not—to a treatment with IRE1 RNase inhibitor.

Prediction Methods and Methods of Treatment of the Invention

A first object of the present invention relates to a method for predicting whether a subject will be eligible to a treatment with an IRE1 RNase inhibitor comprising
i) determining the expression level of at least one gene among ASS1, C3, CCL20, COL4A6, CXCL2, CXCL5, CXCL8, IFI44L, IL1B, IL6, KCNN2, MMP1, MMP12, MMP3, PLA2G4A, PPP4R4, SERPINB2, TFPI2, ZNF804A, ANGPT1, CFH, CFI, CLEC3B, COL3A1, COL8A1, DACH1, DCN, FHL1, GAS1, LUM, OXTR, PLAC8, RGS4, TAGLN, TGFB2, THBS1, TIMP3 and TMEM255A in a sample obtained from the subject, ii) comparing the expression level of each gene determined a step i) with its respective predetermined reference level and iii) and concluding that the subject will be eligible to a treatment with an inhibitor of IRE1 RNAse when the level determined at step i) for at least one gene among ASS1, C3, CCL20, COL4A6, CXCL2, CXCL5, CXCL8, IFI44L, IL1B, IL6, KCNN2, MMP1, MMP12, MMP3, PLA2G4A, PPP4R4, SERPINB2, TFPI2 and ZNF804A is lower than the respective predetermined reference level and the level determined at step i) for at least one gene among ANGPT1, CFH, CFI, CLEC3B, COL3A1, COL8A1, DACH1, DCN, FHL1, GAS1, LUM, OXTR, PLAC8, RGS4, TAGLN, TGFB2, THBS1, TIMP3 and TMEM255A is higher than its predetermined reference level, or concluding that the subject will be eligible to a treatment with an inhibitor of IRE1 RNase when the level determined at step i) for at least one gene among ASS1, C3, CCL20, COL4A6, CXCL2, CXCL5, CXCL8, IFI44L, IL1B, IL6, KCNN2, MMP1, MMP12, MMP3, PLA2G4A, PPP4R4, SERPINB2, TFPI2 and ZNF804A is higher than the respective predetermined reference level and the level determined at step i) for at least one gene among ANGPT1, CFH, CFI, CLEC3B, COL3A1, COL8A1, DACH1, DCN, FHL1, GAS1, LUM, OXTR, PLAC8, RGS4, TAGLN, TGFB2, THBS1, TIMP3 and TMEM255A is lower than its predetermined reference level.

As used herein, the term "ASS1" refer to Argininosuccinate synthetase 1 gene, which encodes for the Argininosuccinate synthetase enzyme (NCBI gene reference ID for *Homo sapiens:* 445; Uniprot reference for *Homo sapiens*: P00966).

As used herein, the term "C3" refer to Complement component 3 gene, which encodes for the Complement component 3 (NCBI gene reference ID for *Homo sapiens:* 718; Uniprot reference for *Homo sapiens*: P01024).

As used herein, the term "CCL20" refer to Chemokine ligand 20 gene, which encodes for the Chemokine (C-C motif) ligand 20 (NCBI gene reference ID for *Homo sapiens:* 6364; Uniprot reference for *Homo sapiens*: P78556).

As used herein, the term "COL4A6" refer to gene which encodes for the Collagen alpha-6(IV) chain (NCBI gene reference ID for *Homo sapiens:* 1288; Uniprot reference for *Homo sapiens*: Q14031).

As used herein, the term "CXCL2" refer to gene which encodes for Chemokine (C-X-C motif) ligand 2 (NCBI gene reference ID for *Homo sapiens:* 2920; Uniprot reference for *Homo sapiens*: P19875).

As used herein, the term "CXCL5" refer to gene which encodes for C-X-C motif chemokine 5 (NCBI gene reference ID for *Homo sapiens:* 6374; Uniprot reference for *Homo sapiens*: P42830).

As used herein, the term "CXCL8" refer to gene which encodes for Interleukin 8 or chemokine (C-X-C motif) ligand 8 (NCBI gene reference ID for *Homo sapiens:* 3576; Uniprot reference for *Homo sapiens*: P10145).

As used herein, the term "IFI44L" refer to gene which encodes for Interferon-induced protein 44-like (NCBI gene reference ID for *Homo sapiens:* 10964; Uniprot reference for *Homo sapiens*: C9JPJ0).

As used herein, the term "IL1B" refer to gene which encodes for Interleukin-1 beta (NCBI gene reference ID for *Homo sapiens:* 3553; Uniprot reference for *Homo sapiens*: P01584).

As used herein, the term "IL6" refer to gene which encodes for interleukin 6 (NCBI gene reference ID for *Homo sapiens:* 3569; Uniprot reference for *Homo sapiens*: P05231).

As used herein, the term "KCNN2" refer to gene which encodes for Potassium intermediate/small conductance calcium-activated channel, subfamily N, member 2 (NCBI gene reference ID for *Homo sapiens:* 3781; Uniprot reference for *Homo sapiens*: Q9H2S1).

As used herein, the term "MMP1" refer to gene which encodes for Matrix metalloproteinase-1 (NCBI gene reference ID for *Homo sapiens:* 4312; Uniprot reference for *Homo sapiens*: P03956).

As used herein, the term "MMP12" refer to gene which encodes for Matrix metalloproteinase-12 (NCBI gene reference ID for *Homo sapiens:* 4321; Uniprot reference for *Homo sapiens*: P39900).

As used herein, the term "MMP3" refer to gene which encodes for matrix metalloproteinase-3 (NCBI gene reference ID for *Homo sapiens:* 4314; Uniprot reference for *Homo sapiens*: P08254).

As used herein, the term "PLA2G4A" refer to gene which encodes for Cytosolic phospholipase A2 (NCBI gene reference ID for *Homo sapiens:* 5321; Uniprot reference for *Homo sapiens*: P47712).

As used herein, the term "PPP4R4" refer to gene which encodes for Serine/threonine-protein phosphatase 4 regulatory subunit 4 (NCBI gene reference ID for *Homo sapiens:* 57718; Uniprot reference for *Homo sapiens*: Q6NUP7).

As used herein, the term "SERPINB2" refer to gene which encodes for Plasminogen activator inhibitor-2 (NCBI gene reference ID for *Homo sapiens:* 5055; Uniprot reference for *Homo sapiens*: P05120).

As used herein, the term "TFPI2" refer to gene which encodes for Tissue factor pathway inhibitor 2 (NCBI gene reference ID for *Homo sapiens:* 7980; Uniprot reference for *Homo sapiens*: P48307).

As used herein, the term "ZNF804A" refer to gene which encodes for Zinc finger protein 804A (NCBI gene reference ID for *Homo sapiens:* 91752; Uniprot reference for *Homo sapiens*: Q7Z570).

As used herein, the term "ANGPT1" refer to gene which encodes for Angiopoietin 1 (NCBI gene reference ID for *Homo sapiens:* 284; Uniprot reference for *Homo sapiens*: Q15389).

As used herein, the term "CFH" refer to gene which encodes for complement factor H (NCBI gene reference ID for *Homo sapiens:* 3075; Uniprot reference for *Homo sapiens*: P08603).

As used herein, the term "CFI" refer to gene which encodes for complement factor I (NCBI gene reference ID for *Homo sapiens:* 3426; Uniprot reference for *Homo sapiens*: P05156).

As used herein, the term "CLEC3B" refer to gene which encodes for Tetranectin (NCBI gene reference ID for *Homo sapiens:* 7123; Uniprot reference for *Homo sapiens*: P05452).

As used herein, the term "COL3A1" refer to gene which encodes for collagen type III alpha 1 chain (NCBI gene reference ID for *Homo sapiens:* 1281; Uniprot reference for *Homo sapiens*: P02461).

As used herein, the term "COL8A1" refer to gene which encodes for collagen type VIII alpha 1 chain (NCBI gene reference ID for *Homo sapiens:* 1295; Uniprot reference for *Homo sapiens*: P27658).

As used herein, the term "DACH1" refer to gene which encodes for dachshund family transcription factor 1 (NCBI gene reference ID for *Homo sapiens:* 1602; Uniprot reference for *Homo sapiens:* Q9UI36).

As used herein, the term "DCN" refer to gene which encodes for Decorin (NCBI gene reference ID for *Homo sapiens:* 1634; Uniprot reference for *Homo sapiens:* P07585).

As used herein, the term "FHL1" refer to gene which encodes for Four and a half LIM domains protein 1 (NCBI gene reference ID for *Homo sapiens:* 2273; Uniprot reference for *Homo sapiens:* Q13642/Q5JXH9).

As used herein, the term "GAS1" refer to gene which encodes for Growth arrest-specific protein 1 (NCBI gene reference ID for *Homo sapiens:* 2619; Uniprot reference for *Homo sapiens:* P54826).

As used herein, the term "LUM" refer to gene which encodes for Lumican (NCBI gene reference ID for *Homo sapiens:* 4060; Uniprot reference for *Homo sapiens:* P51884).

As used herein, the term "OXTR" refer to gene which encodes for oxytocin receptor (NCBI gene reference ID for *Homo sapiens:* 5021; Uniprot reference for *Homo sapiens:* P30559).

As used herein, the term "PLAC8" refer to gene which encodes for placenta specific 8 (NCBI gene reference ID for *Homo sapiens:* 51316; Uniprot reference for *Homo sapiens:* Q9NZF1).

As used herein, the term "RGS4" refer to gene which encodes for Regulator of G protein signaling 4 (NCBI gene reference ID for *Homo sapiens:* 5999; Uniprot reference for *Homo sapiens:* P49798).

As used herein, the term "TAGLN" refer to gene which encodes for Transgelin (NCBI gene reference ID for *Homo sapiens:* 6876; Uniprot reference for *Homo sapiens:* Q01995).

As used herein, the term "TGFB2" refer to gene which encodes for Transforming growth factor-beta 2 (NCBI gene reference ID for *Homo sapiens:* 7042; Uniprot reference for *Homo sapiens:* P61812).

As used herein, the term "THBS1" refer to gene which encodes for Thrombospondin 1 (NCBI gene reference ID for *Homo sapiens:* 7057; Uniprot reference for *Homo sapiens:* P07996).

As used herein, the term "TIMP3" refer to gene which encodes for Metalloproteinase inhibitor 3 (NCBI gene reference ID for *Homo sapiens:* 7078; Uniprot reference for *Homo sapiens:* P35625).

As used herein, the term "TMEM255A" refer to gene which encodes for Transmembrane protein 255A (NCBI gene reference ID for *Homo sapiens:* 55026; Uniprot reference for *Homo sapiens:* Q5JRV8).

Another object of the present invention relates to a method of treating cancer in a subject in need thereof comprising i) predicting whether a subject will be eligible to a treatment with an IRE1 RNase inhibitor by performing the method of the invention and ii) administering to the subject a therapeutically effective amount of an IRE1 RNase inhibitor when it is concluded that the subject will be eligible to a treatment with an IRE1 RNase inhibitor.

As used herein, the term "subject" denotes a mammal, such as a rodent, a feline, a canine, and a primate. Preferably, a subject according to the invention is a human. In one embodiment, the subject suffering from cancer.

The terms "cancer" has its general meaning in the art and refers to a group of diseases involving abnormal cell growth with the potential to invade or spread to other parts of the body. The term "cancer" further encompasses both primary and metastatic cancers. Examples of cancers that may be treated by methods and compositions of the invention include, but are not limited to, cancer cells from the bladder, blood, bone, bone marrow, brain, breast, colon, esophagus, gastrointestinal, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis *coli*; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; non encapsulating sclerosing carcinoma; adrenal cortical carcinoma; endometroid carcinoma; skin appendage carcinoma; apocrine adenocarcinoma; sebaceous adenocarcinoma; ceruminous; adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; Sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malign melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brennertumor, malignant; phyllodestumor, malignant; synovial sarcoma; mesothelioma, malignant; dysgerminoma; embryonal carcinoma; teratoma, malignant; strumaovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblasticodontosarcoma; ameloblastoma, malignant; ameloblasticfibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocyticleukemia; mast cell leukemia; megakaryoblasticleukemia; myeloid sarcoma; and hairy cell leukemia.

In some embodiments, the subject suffers from a cancer selected from the group consisting of bile duct cancer, bladder cancer, bone cancer, brain and central nervous system cancer, breast cancer, Castleman disease cervical cancer, colorectal cancer, endometrial cancer, esophagus cancer, gallbladder cancer, gastrointestinal carcinoid tumors, Hodgkin's disease, non-Hodgkin's lymphoma, Kaposi's sarcoma, kidney cancer, laryngeal and hypopharyngeal cancer, liver cancer, lung cancer, mesothelioma, plasmacytoma, nasal cavity and paranasal sinus cancer, nasopharyngeal cancer, neuroblastoma, oral cavity and oropharyngeal cancer, ovarian cancer, pancreatic cancer, penile cancer, pituitary cancer, prostate cancer, retinoblastoma, rhabdomyosarcoma, salivary gland cancer, skin cancer, stomach cancer, testicular cancer, thymus cancer, thyroid cancer, vaginal cancer, vulvar cancer, and uterine cancer.

In one embodiment, cancer is glioblastoma.

As used herein, the term glioblastoma (GBM), also called glioblastoma multiforme or "grade IV astrocytoma" according to WHO classification, has its general meaning in the art and refers to central nervous system primary tumor derived from glial cells. GBM is one of the deadliest human cancers with an incidence of about 3.5/100,000 per year worldwide (Cloughesy, T. F., W. K. Cavenee, and P. S. Mischel, Glioblastoma: from molecular pathology to targeted treatment. Annu Rev Pathol, 2014. 9: p. 1-25). Despite the aggressive standard of care currently used including surgery, chemo- and radiotherapy, the prognosis remains very poor with ~15 months overall survival (Weathers, S. P. and M. R. Gilbert, Advances in treating glioblastoma. F1000Prime Rep, 2014. 6: p. 46).

In one embodiment, cancer is melanoma.

As used herein, the term "melanoma" refers to all types of melanoma, including, cutaneous melanoma, extracutaneous melanoma, superficial spreading melanoma, malignant melanoma, nodular melanoma, nodular malignant melanoma, polypoid melanoma, acral lentiginous melanoma, lentiginous malignant melanoma, lentigo maligna melanoma, mucosal lentignous melanoma, mucosal melanoma, soft-tissue melanoma, and desmoplastic melanoma. The term "melanoma" includes primary melanoma and metastatic melanoma In one embodiment, cancer is colorectal cancer.

The term "colorectal cancer", also known as "colon cancer", "rectal cancer", or "bowel cancer", refers to a cancer from uncontrolled cell growth in the colon or rectum, or in the appendix. The term is used to refer to adenocarcinomas, carcinoid tumors, Gastrointestinal stromal tumors (GISTs) or sarcomas. As used herein, the term colorectal cancer refers to stage I, stage IIA, stage IIB, stage IIC, stage IIIA, stage IIIB, stage IIIC, stage IVA or stage IVB colorectal cancer Moreover, as used herein, colorectal cancer refers both to primary colorectal tumors as well as to secondary colorectal cancer, i.e. a colorectal cancer which results from the metastasis from a primary cancer elsewhere in the body.

As used herein, the term "sample" refers to any substance of biological origin. Examples of samples includes, but are not limited to blood, tumor, saliva, urine, cerebrospinal fluids, or any of other biological fluids or tissues.

In a preferred embodiment, the sample is tumor sample. As used herein, the term "tumor sample" means any tissue tumor sample derived from the subject. Said tissue sample is obtained for the purpose of the in vitro evaluation. In some embodiments, the tumor sample may result from the tumor resected from the subject. In some embodiments, the tumor sample may result from a biopsy performed in the primary tumor of the subject or performed in metastatic sample distant from the primary tumor of the subject. In some embodiments, the tumor sample is a sample of circulating tumor cells. As used herein, the term "circulating tumor cell" or "CTC" refers to a cancer cell derived from a cancerous tumor that has detached from the tumor and is circulating in the blood stream of the subject. Typically the CTCs are isolated from the blood sample using a filter and/or a marker based method.

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread of the disease, preventing or delaying the recurrence of the disease, delaying or slowing the progression of the disease, ameliorating the disease state, providing a remission (partial or total) of the disease, decreasing the dose of one or more other medications required to treat the disease, delaying the progression of the disease, increasing the quality of life, and/or prolonging survival. The term "treatment" encompasses the prophylactic treatment. As used herein, the term "prevent" refers to the reduction in the risk of acquiring or developing a given condition.

As used herein, "therapeutically effective amount" means a sufficient amount of an IRE1 RNase inhibitor for use in a method for the treatment of cancer at a reasonable benefit/risk ratio applicable to any medical treatment. It will be understood that the total daily usage of the compounds and compositions of the present invention will be decided by the attending physician within the scope of sound medical judgment. The specific therapeutically effective dose level for any particular subject will depend upon a variety of factors including the severity of cancer, the age, body weight, general health, sex and diet of the subject; the time of administration, route of administration, and rate of excretion of the specific compound employed; the duration of the treatment; and like factors well known in the medical arts. For example, it is well known within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Typically, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, typically from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

The terms "administer" or "administration" refer to the act of injecting or otherwise physically delivering a substance as it exists outside the body (e.g., IRE1 RNase inhibitor) into the subject. When a disease, or a symptom thereof, is being treated, administration of the substance typically occurs after the onset of the disease or symptoms thereof. When a disease or symptoms thereof, are being prevented, administration of the substance typically occurs before the onset of the disease or symptoms thereof.

As used herein, the term "predicting" refers to a probability or likelihood for a patient to respond to the treatment with an IRE1 RNase inhibitor. As used herein, the term "responsiveness" refers to ability to assess the likelihood that treatment will or will not be clinically effective.

As used herein, the term "predetermined reference level" refers to the expression levels of ASS1, C3, CCL20, COL4A6, CXCL2, CXCL5, CXCL8, IFI44L, IL1B, IL6, KCNN2, MMP1, MMP12, MMP3, PLA2G4A, PPP4R4, SERPINB2, TFPI2, ZNF804A, ANGPT1, CFH, CFI, CLEC3B, COL3A1, COL8A1, DACH1, DCN, FHL1, GAS1, LUM, OXTR, PLAC8, RGS4, TAGLN, TGFB2, THBS1, TIMP3 and TMEM255A in samples obtained from the general population or from a selected population of subjects (tumor specimens from patients suffering from cancer). A "predetermined reference level" may be determined, for example, by determining the expression level of ASS1, C3, CCL20, COL4A6, CXCL2, CXCL5, CXCL8, IFI44L, IL1B, IL6, KCNN2, MMP1, MMP12, MMP3, PLA2G4A, PPP4R4, SERPINB2, TFPI2, ZNF804A, ANGPT1, CFH, CFI, CLEC3B, COL3A1, COL8A1, DACH1, DCN, FHL1, GAS1, LUM, OXTR, PLAC8, RGS4, TAGLN, TGFB2, THBS1, TIMP3 and TMEM255A nucleic acids or encoded polypeptides, in a corresponding sample obtained from one or more control subject(s). When such a predetermined reference level is used, a higher or increased levels determined in a sample (i.e. a test sample obtained from the subject) is indicative for example that said patient is eligible to a treatment with an IRE1 RNase inhibitor.

As used herein, the term "RNase activity of IRE1" refers to the activity of the endoribonuclease domain of IRE1 which either degrades specific RNA (mRNA or microRNA) to avoid their translation or their cellular activity (in the case of microRNA), an activity known as the RIDD (regulated IRE1-dependent decay of RNA), or contributes to the splicing XBP1 (X-box-binding protein 1) mRNA to change the reading frame leading to the production of a novel protein (XBP1s), a potent unfolded-protein response transcriptional activator.

As used herein, the term "inhibitor of RNase activity of IRE1" has its general meaning in the art and refers to any compound, natural or synthetic, that blocks, suppresses, or reduces (including significantly) the RNase activity of IRE1. The term "inhibitor of RNase activity of IRE1" includes but is not limited to: small organic molecule, polypeptide, peptidomimetics.

Tests for determining the capacity of a compound to be inhibitor of RNase activity of IRE1 are well known to the person skilled in the art. Inhibition of the RNase activity of IRE1 may be determined by any techniques well known in the art. For instance, an inhibitor of RNase activity of IRE1 can be identified by carrying out the following steps: i) providing a plurality of test substances ii) determining whether the test substances are inhibitors of RNase activity of IRE1 and iii) positively selecting the test substances that are inhibitor of RNase activity of IRE1. The test substances that have been positively selected may be subjected to further selection steps in view of further assaying its properties for the treatment of cancer. For example, the candidate compounds that have been positively selected may be subjected to further selection steps in view of further assaying its properties on animal models.

The assays may be performed using high throughput screening techniques for identifying test substances for developing drugs (inhibitor of IRE1 RNase activity) that may be useful to the treatment of cancer. High throughput screening techniques may be carried out using multi-well plates (e.g., 96-, 389-, or 1536-well plates), in order to carry out multiple assays using an automated robotic system. Thus, large libraries of test substances may be assayed in a highly efficient manner. Compounds in the library will be applied one at a time in an automated fashion to the wells of the microtitre dishes. Once the test substances which inhibits the RNase activity of IRE1 are identified, they can be positively selected for further characterization. Because this assay can readily be performed in a microtitre plate format, the assays described can be performed by an automated robotic system, allowing for testing of large numbers of test samples within a reasonably short time frame. The assays can be used as a screen to assess the activity of a previously untested compound or extract, in which case a single concentration is tested and compared to controls. These assays can also be used to assess the relative potency of a compound by testing a range of concentrations, in a range of 100 µM to 1 µM, for example, and computing the more efficient concentration.

In some embodiments, the RNase activity of IRE1 inhibitor is a small organic molecule. The term "small organic molecule" refers to a molecule of a size comparable to those organic molecules generally used in pharmaceuticals. The term excludes biological macromolecules (e.g., proteins, nucleic acids, etc.). Preferred small organic molecules range in size up to about 5000 Da, more in particular up to 2000 Da, and most in particular up to about 1000 Da.

In one embodiment, the inhibitor of the RNase activity of IRE1α is a RNase domain inhibitor.

In one embodiment, the inhibitor of the RNase activity of IRE1α is a kinase inhibitor.

In one embodiment, the inhibitor of the RNase activity of IRE1α is a type I kinase inhibitor. In one embodiment, the inhibitor of the RNase activity of IRE1α is type II kinase inhibitor.

In a particular embodiment, the inhibitor of the RNase activity of IRE1α is STF083010.

As used herein, the term "STF083010" has its general meaning in the art and refers to N-[(2-Hydroxy-1-naphthalenyl)methylene]-2-thiophenesulfonamide.

In one embodiment, the inhibitor of the RNase activity of IRE1α is 4µ8c.

In one embodiment, the inhibitor of the RNase activity of IRE1α is Irestatin.

In one embodiment, the inhibitor of the RNase activity of IRE1α is MG132.

In one embodiment, the inhibitor of the RNase activity of IRE1α is 17-AAG.

In one embodiment, the inhibitor of the RNase activity of IRE1α is 1-NM-PP1.

In one embodiment, the inhibitor of the RNase activity of IRE1α is Lactacystin.

In one embodiment, the inhibitor of the RNase activity of IRE1α is MKC-3946.

In one embodiment, the inhibitor of the RNase activity of IRE1α is toyocamycin.

In one embodiment, the inhibitor of the RNase activity of IRE1α is 3-methoxy-6-bromosalicylaldehyde.

In one embodiment, the inhibitor of the RNase activity of IRE1α is APY29.

In one embodiment, the inhibitor of the RNase activity of IRE1α is sunitinib.

In one embodiment, the inhibitor of the RNase activity of IRE1α is KIRA6.

In one embodiment, the inhibitor of the RNase activity of IRE1α is a 4-phenylbutyric acid analogue (Zhang H, Nakajima S, Kato H, Gu L, Yoshitomi T, Nagai K, et al. Selective, potent blockade of the IRE1 and ATF6 pathways by 4-phenylbutyric acid analogues. Br J Pharmacol. October 2013; 170(4):822-34).

In some embodiments, the RNase activity of IRE1 inhibitor is a polypeptide or fragment thereof.

The term "polypeptide" refers both short peptides with a length of at least two amino acid residues and at most 10 amino acid residues, oligopeptides (11-100 amino acid residues), and longer peptides (the usual interpretation of "polypeptide", i.e. more than 100 amino acid residues in length) as well as proteins (the functional entity comprising at least one peptide, oligopeptide, or polypeptide which may be chemically modified by being glycosylated, by being lipidated, or by comprising prosthetic groups).

The polypeptides of the invention may be produced by any suitable means, as will be apparent to those of skill in the art. In order to produce sufficient amounts of polypeptides for use in accordance with the present invention, expression may conveniently be achieved by culturing under appropriate conditions recombinant host cells containing the polypeptide of the invention. In particular, the polypeptide is produced by recombinant means, by expression from an encoding nucleic acid molecule. Systems for cloning and expression of a polypeptide in a variety of different host cells are well known. When expressed in recombinant form, the polypeptide is in particular generated by expression from an encoding nucleic acid in a host cell. Any host cell may be used, depending upon the individual requirements of a particular system. Suitable host cells include bacteria mammalian cells, plant cells, yeast and baculovirus systems. Mammalian cell lines available in the art for expression of a heterologous polypeptide include Chinese hamster ovary cells. HeLa cells, baby hamster kidney cells and many others. Bacteria are also preferred hosts for the production of recombinant protein, due to the ease with which bacteria may be manipulated and grown. A common, preferred bacterial host is *E. coli*.

The polypeptides of the invention and fragments thereof according to the invention can exhibit post-translational modifications, including, but not limited to glycosylations, (e.g., N-linked or O-linked glycosylations), myristylations, palmitylations, acetylations and phosphorylations (e.g., serine/threonine or tyrosine).

In some embodiments, it is contemplated that polypeptides used in the therapeutic methods of the present invention may be modified in order to improve their therapeutic efficacy. Such modification of therapeutic compounds may be used to decrease toxicity, increase circulatory time, or modify biodistribution. For example, the toxicity of potentially important therapeutic compounds can be decreased significantly by combination with a variety of drug carrier vehicles that modify biodistribution. In example adding dipeptides can improve the penetration of a circulating agent in the eye through the blood retinal barrier by using endogenous transporters.

In some embodiments, the RNase activity of IRE1 inhibitor is a pepetidomimetics.

As used herein the term "peptidomimetic" means a peptide-like molecule that has the activity of the peptide upon which it is structurally based. Such peptidomimetics include chemically modified peptides, peptide-like molecules containing non-naturally occurring amino acids, and peptoids, and have an activity such as selective homing activity of the peptide upon which the peptidomimetic is derived (see, for example, Goodman and Ro, Peptidomimetics for Drug Design, in "Burger's Medicinal Chemistry and Drug Discovery" Vol. 1 (ed. M. E. Wolff; John Wiley & Sons 1995), pages 803-861). Peptidomimetics may be designed in order to increase peptide stability, bioavailability, solubility, etc.

Methods for Determining the Expression Level of ASS1, C3, CCL20, COL4A6, CXCL2, CXCL5, CXCL8, IFI44L, IL1B, IL6, KCNN2, MMP1, MMP12, MMP3, PLA2G4A, PPP4R4, SERPINB2, TFPI2, ZNF804A, ANGPT1, CFH, CFI, CLEC3B, COL3A1, COL8A1, DACH1, DCN, FHL1, GAS1, LUM, OXTR, PLAC8, RGS4, TAGLN, TGFB2, THBS1, TIMP3 and TMEM255A:

Determination of the expression level of ASS1, C3, CCL20, COL4A6, CXCL2, CXCL5, CXCL8, IFI44L, IL1B, IL6, KCNN2, MMP1, MMP12, MMP3, PLA2G4A, PPP4R4, SERPINB2, TFPI2, ZNF804A, ANGPT1, CFH, CFI, CLEC3B, COL3A1, COL8A1, DACH1, DCN, FHL1, GAS1. LUM, OXTR, PLAC8, RGS4, TAGLN, TGFB2, THBS1, TIMP3 and TMEM255A genes may be performed by a variety of techniques. Generally, the expression level as determined is a relative expression level. For example, the determination comprises contacting the sample with selective reagents such as probes or ligands, and thereby detecting the presence, or measuring the amount, of nucleic acids or polypeptides of interest originally in said sample. Contacting may be performed in any suitable device, such as a plate, microtiter dish, test tube, well, glass, column, and so forth. In specific embodiments, the contacting is performed on a substrate coated with the reagent, such as a nucleic acid array or a specific ligand array. The substrate may be a solid or semi-solid substrate such as any suitable support comprising glass, plastic, nylon, paper, metal, polymers and the like. The substrate may be of various forms and sizes, such as a slide, a membrane, a bead, a column, a gel, etc. The contacting may be made under any condition suitable for a detectable complex, such as a nucleic acid hybrid or an antibody-antigen complex, to be formed between the reagent and the nucleic acids or polypeptides of the biological sample.

In a particular embodiment of the invention, the expression level of ASS1, C3, CCL20, COL4A6, CXCL2, CXCL5, CXCL8, IFI44L, IL1B, IL6, KCNN2, MMP1, MMP12, MMP3, PLA2G4A, PPP4R4, SERPINB2, TFPI2, ZNF804A, ANGPT1, CFH, CFI, CLEC3B, COL3A1, COL8A1, DACH1, DCN, FHL1, GAS1, LUM, OXTR, PLAC8, RGS4, TAGLN, TGFB2, THBS1, TIMP3 and TMEM255A genes may be determined by determining the quantity of mRNA.

Methods for determining the quantity of mRNA are well known in the art. For example the nucleic acid contained in the samples is first extracted according to standard methods, for example using lytic enzymes or chemical solutions or extracted by nucleic-acid-binding resins following the manufacturer's instructions. The extracted mRNA is then detected by hybridization (e.g., Northern blot analysis) and/ or amplification (e.g., RT-PCR). Quantitative or semi-quantitative RT-PCR is preferred. Real-time quantitative or semi-quantitative RT-PCR is particularly advantageous.

Nucleic acids having at least 10 nucleotides and exhibiting sequence complementarity or homology to the mRNA of interest herein find utility as hybridization probes. It is understood that such nucleic acids need not be identical, but are typically at least about 80% identical to the homologous region of comparable size, more preferably 85% identical and even more preferably 90-95% identical. Probes typically comprise single-stranded nucleic acids of between 10 to 1000 nucleotides in length, for instance of between 10 and 800, more preferably of between 15 and 700, typically of between 20 and 500. The probes and primers are "specific" to the nucleic acids they hybridize to, i.e. they preferably hybridize under high stringency hybridization conditions (corresponding to the highest melting temperature Tm, e.g., 50% formamide, 5× or 6×SCC. SCC is a 0.15 M NaCl, 0.015 M Na-citrate).

In the context of the invention, "hybridization" relates to the fact of obtaining a close interaction of the nucleotide probe and the target region that is expected to be revealed by the detection of the nucleotide probe. Such an interaction can be achieved by the formation of hydrogen bonds between the nucleotide probe and the target sequence, which is typical of the interactions between complementary nucleotide molecules capable of base pairing. Hydrogen bonds can be found, for example, in the annealing of two complementary strands of DNA.

It will be advantageous to use nucleic acids in combination with appropriate means, such as a detectable label, for detecting hybridization. A wide variety of appropriate indicators are known in the art including, fluorescent, radioactive, enzymatic or other ligands.

Conventional methods and reagents for isolating RNA from a sample comprise High Pure miRNA Isolation Kit (Roche), Trizol (Invitrogen), Guanidinium thiocyanate-phenol-chloroform extraction, PureLink™ miRNA isolation kit (Invitrogen), PureLink Micro-to-Midi Total RNA Purification System (invitrogen), RNeasy kit (Qiagen), Oligotex kit (Qiagen), phenol extraction, phenol-chloroform extraction, TCA/acetone precipitation, ethanol precipitation, Column purification, Silica gel membrane purification, PureYield™ RNA Midiprep (Promega), PolyATtract System 1000 (Promega), Maxwell® 16 System (Promega), SV Total RNA Isolation (Promega), geneMAG-RNA/DNA kit (Chemicell), TRI Reagent® (Ambion), RNAqueous Kit (Ambion), ToTALLY RNA™ Kit (Ambion), Poly(A)Purist™ Kit (Ambion) and any other methods, commercially available or not, known to the skilled person.

In one embodiment, the expression level of one or more mRNAs is determined by the quantitative polymerase chain reaction (QPCR) technique. The QPCR may be performed using chemicals and/or machines from a commercially available platform. The QPCR may be performed using QPCR machines from any commercially available platform; such as Prism, geneAmp or StepOne Real Time PCR systems (Applied Biosystems), LightCycler (Roche), RapidCycler (Idaho Technology), MasterCycler (Eppendorf), BioMark™ HD System (Fluidigm), iCycler iQ system, Chromo 4 system, CFX, MiniOpticon and Opticon systems (Bio-Rad), SmartCycler system (Cepheid), RotorGene system (Corbett Lifescience), MX3000 and MX3005 systems (Stratagene), DNA Engine Opticon system (Qiagen), Quantica qPCR systems (Techne), InSyte and Syncrom cycler system (BioGene), DT-322 (DNA Technology), Exicycler Notebook Thermal cycler, TL998 System (lanlong), Line-Gene-K systems (Bioer Technology), or any other commercially available platform. The QPCR may be performed using chemicals from any commercially available platform, such as NCode EXPRESS qPCR or EXPRESS qPCR (Invitrogen), Taqman or SYBR green qPCR systems (Applied Biosystems), Real-Time PCR reagents (Eurogentec), iTaq mix (Bio-Rad), qPCR mixes and kits (Biosense), and any other chemicals, commercially available or not, known to the skilled person. The QPCR reagents and detection system may be probe-based, or may be based on chelating a fluorescent chemical into double-stranded oligonucleotides.

The QPCR reaction may be performed in a tube; such as a single tube, a tube strip or a plate, or it may be performed in a microfluidic card in which the relevant probes and/or primers are already integrated.

In a particular embodiment, the expression level of ASS1, C3, CCL20, COL4A6, CXCL2, CXCL5, CXCL8, IFI44L, IL1B, IL6, KCNN2, MMP1, MMP12, MMP3, PLA2G4A, PPP4R4, SERPINB2, TFPI2, ZNF804A, ANGPT1, CFH, CFI, CLEC3B, COL3A1, COL8A1, DACH1, DCN, FHL1, GAS1, LUM, OXTR, PLAC8, RGS4, TAGLN, TGFB2, THBS1, TIMP3 and TMEM255A genes may be determined by determining of the quantity of protein encoded by the ASS1, C3, CCL20, COL4A6, CXCL2, CXCL5, CXCL8, IFI44L, IL1B, IL6, KCNN2, MMP1, MMP12, MMP3, PLA2G4A, PPP4R4, SERPINB2, TFPI2, ZNF804A, ANGPT1, CFH, CFI, CLEC3B, COL3A1, COL8A1, DACH1, DCN, FHL1, GAS1, LUM, OXTR, PLAC8, RGS4, TAGLN, TGFB2, THBS1, TIMP3 and TMEM255A genes.

Such methods comprise contacting the sample with a binding partner capable of selectively interacting with the protein present in said sample. The binding partner is generally an antibody that may be polyclonal or monoclonal, preferably monoclonal.

As used herein, the term "monoclonal antibody" refers to a population of antibody molecules that contains only one species of antibody combining site capable of immunoreacting with a particular epitope. A monoclonal antibody thus typically displays a single binding affinity for any epitope with which it immunoreacts. A monoclonal antibody may therefore contain an antibody molecule having a plurality of antibody combining sites, each immunospecific for a different epitope, e.g. a bispecific monoclonal antibody.

Laboratory methods for preparing monoclonal antibodies are well known in the art (see, for example, Harlow et al., 1988). Monoclonal antibodies (mAbs) may be prepared by immunizing purified CD90 into a mammal, e.g. a mouse, rat and the like mammals. The antibody-producing cells in the immunized mammal are isolated and fused with myeloma or heteromyeloma cells to produce hybrid cells (hybridoma). The hybridoma cells producing the monoclonal antibodies are utilized as a source of the desired monoclonal antibody. This standard method of hybridoma culture is described in Kohler and Milstein (1975).

While mAbs can be produced by hybridoma culture the invention is not to be so limited. Also contemplated is the use of mAbs produced by an expressing nucleic acid cloned from a hybridoma of this invention. That is, the nucleic acid expressing the molecules secreted by a hybridoma of this invention can be transferred into another cell line to produce a transformant. The transformant is genotypically distinct from the original hybridoma but is also capable of producing antibody molecules of this invention, including immunologically active fragments of whole antibody molecules, corresponding to those secreted by the hybridoma. See, for example, U.S. Pat. No. 4,642,334 to Reading; European Patent Publications No. 0239400 to Winter et al. and No. 0125023 to Cabilly et al.

Antibody generation techniques not involving immunisation are also contemplated such as for example using phage display technology to examine naive libraries (from non-immunised animals); see Barbas et al. (1992), and Waterhouse et al. (1993).

Alternatively, binding agents other than antibodies may be used for the purpose of the invention. These may be for instance aptamers, which are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as E. coli Thioredoxin A that are selected from combinatorial libraries by two hybrid methods (Colas et al., 1996).

The binding partners of the invention such as antibodies or aptamers, may be labelled with a detectable molecule or substance, such as a fluorescent molecule, a radioactive molecule or any others labels known in the art. Labels are known in the art that generally provide (either directly or indirectly) a signal. As used herein, the term "labelled", with regard to the antibody or aptamer, is intended to encompass direct labeling of the antibody or aptamer by coupling (i.e., physically linking) a detectable substance, such as a radioactive agent or a fluorophore (e.g. fluorescein isothiocyanate (FITC) or phycoerythrin (PE) or lndocyanine (Cy5)) to the antibody or aptamer, as well as indirect labelling of the probe or antibody by reactivity with a detectable substance. An antibody or aptamer of the invention may be labelled with a radioactive molecule by any method known in the art.

The aforementioned assays generally involve the coating of the binding partner (ie. antibody or aptamer) in a solid support. Solid supports which can be used in the practice of the invention include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like.

In another embodiment of the invention, the measurement of ASS1, C3, CCL20, COL4A6, CXCL2, CXCL5, CXCL8, IFI44L, IL1B, IL6, KCNN2, MMP1, MMP12, MMP3, PLA2G4A, PPP4R4, SERPINB2, TFPI2, ZNF804A, ANGPT1, CFH, CFI, CLEC3B, COL3A1, COL8A1, DACH1, DCN, FHL1, GAS1, LUM, OXTR, PLAC8, RGS4, TAGLN, TGFB2, THBS1, TIMP3 and TMEM255A in the sample may be achieved by a cytometric bead array system wherein the antibodies that bind to the biomarkers are coated directly or indirectly on beads. Typically, Luminex® technology which is a new technology based on fluorescent detection using a flow cytometer, microbeads dyed with multiple fluorescent colours and lasers detection may be used.

For example, the level of a biomarker protein such as ASS1, C3, CCL20, COL4A6, CXCL2, CXCL5, CXCL8, IFI44L, IL1B, IL6, KCNN2, MMP1, MMP12, MMP3, PLA2G4A, PPP4R4, SERPINB2, TFPI2, ZNF804A, ANGPT1, CFH, CFI, CLEC3B, COL3A1, COL8A1, DACH1, DCN, FHL1, GAS1, LUM, OXTR, PLAC8, RGS4, TAGLN, TGFB2, THBS1, TIMP3 and TMEM255A may be measured by using standard electrophoretic and immunodiagnostic techniques, including immunoassays such as competition, direct reaction, or sandwich type assays. Such assays include, but are not limited to, Western blots; agglutination tests; enzyme-labeled and mediated immunoassays, such as ELISAs; biotin/avidin type assays; radioimmunoassays; Immunoelectrophoresis; immunoprecipitation.

More particularly, an ELISA method can be used, wherein the wells of a microtiter plate are coated with a set of antibodies against ASS1, C3, CCL20, COL4A6, CXCL2, CXCL5, CXCL8, IFI44L, IL1B, IL6, KCNN2, MMP1, MMP12, MMP3, PLA2G4A, PPP4R4, SERPINB2, TFPI2, ZNF804A, ANGPT1, CFH, CFI, CLEC3B, COL3A1, COL8A1, DACH1, DCN, FHL1, GAS1, LUM, OXTR, PLAC8, RGS4, TAGLN, TGFB2, THBS1, TIMP3 and TMEM255A. A sample containing or suspected of containing ASS1, C3, CCL20, COL4A6, CXCL2, CXCL5, CXCL8, IFI44L, IL1B, IL6, KCNN2, MMP1, MMP12, MMP3, PLA2G4A, PPP4R4, SERPINB2, TFPI2, ZNF804A, ANGPT1, CFH, CFI, CLEC3B, COL3A1, COL8A1, DACH1, DCN, FHL1, GAS1, LUM, OXTR, PLAC8, RGS4, TAGLN, TGFB2, THBS1, TIMP3 and TMEM255A is then added to the coated wells. After a period of incubation sufficient to allow the formation of antibody-antigen complexes, the plate(s) can be washed to remove unbound moieties and a detectably labeled secondary binding molecule added. The secondary binding molecule is allowed to react with any captured sample marker protein, the plate washed and the presence of the secondary binding molecule detected using methods well known in the art.

Measuring the level of a biomarker protein such as ASS1, C3, CCL20, COL4A6, CXCL2, CXCL5, CXCL8, IFI44L, IL1B, IL6, KCNN2, MMP1, MMP12, MMP3, PLA2G4A, PPP4R4, SERPINB2, TFPI2, ZNF804A, ANGPT1, CFH, CFI, CLEC3B, COL3A1, COL8A1, DACH1, DCN, FHL1, GAS1, LUM, OXTR, PLAC8, RGS4, TAGLN, TGFB2, THBS1, TIMP3 and TMEM255A (with or without immunoassay-based methods) may also include separation of the proteins: centrifugation based on the protein's molecular weight; electrophoresis based on mass and charge; HPLC based on hydrophobicity; size exclusion chromatography based on size; and solid-phase affinity based on the protein's affinity for the particular solid-phase that is use. Once separated, ASS1, C3, CCL20, COL4A6, CXCL2, CXCL5, CXCL8, IFI44L, IL1B, IL6, KCNN2, MMP1, MMP12, MMP3, PLA2G4A, PPP4R4, SERPINB2, TFPI2, ZNF804A, ANGPT1, CFH, CFI, CLEC3B, COL3A1, COL8A1, DACH1, DCN, FHL1, GAS1, LUM, OXTR, PLAC8, RGS4, TAGLN, TGFB2, THBS1, TIMP3 and TMEM255A may be identified based on the known "separation profile" e.g., retention time, for that protein and measured using standard techniques.

Alternatively, the separated proteins may be detected and measured by, for example, a mass spectrometer.

Kits of the Invention

A further object of the invention is a kit suitable for predicting whether a subject will be eligible to a treatment with an IRE1 RNase inhibitor, comprising:

At least a means for determining the expression level of at least one gene among ASS1, C3, CCL20, COL4A6, CXCL2, CXCL5, CXCL8, IFI44L, IL1B, IL6, KCNN2, MMP1, MMP12, MMP3, PLA2G4A, PPP4R4, SERPINB2, TFPI2, ZNF804A, ANGPT1, CFH, CFI, CLEC3B, COL3A1, COL8A1, DACH1, DCN, FHL1, GAS1, LUM, OXTR, PLAC8, RGS4, TAGLN, TGFB2, THBS1, TIMP3 and TMEM255A in a sample obtained from a subject, Instructions for use.

Typically the kit may include primers, probes, an antibody, or a set of antibodies. In a particular embodiment, the antibody or set of antibodies are labelled. The kit may also contain other suitably packaged reagents and materials needed for the particular detection protocol, including solid-phase matrices, if applicable, and standards.

The invention will be further illustrated by the following figures and examples. However, these examples and figures should not be interpreted in any way as limiting the scope of the present invention.

FIGURES

FIG. 1: Bioinformatics workflow for the identification of 38-hub genes representative of the IRE1 signature. Raw data (*.CEL files) from the GSE27306 dataset were processed into R/Bioconductor by using the RMA normalization and Limma package, and 1051 differentially expressed (D.E.) genes were selected between DN and WT U87 cells by using a corrected P value (pval) threshold of 0.05 and fold change threshold of |log 2(F.C.)|≥1.5. D.E. gene list was then introduced into the BioInfoMiner and gene prioritization was executed based on the biomedical ontologies of four different functional and phenotype databases including GO, Reactome, MGI and HPO, separately. For the annotation process was used the "complete" version (see materials and methods) and the hypergeometric pvalue threshold was set to 0.05. Two-hundred twenty-seven (227) highly prioritized genes including their proximal interactors corresponded to the union of the BioInfoMiner output from the four databases and 38 hub-genes were highlighted as the intersection with the IRE1 signature of (Pluquet et al, 2013).

Figure 2:
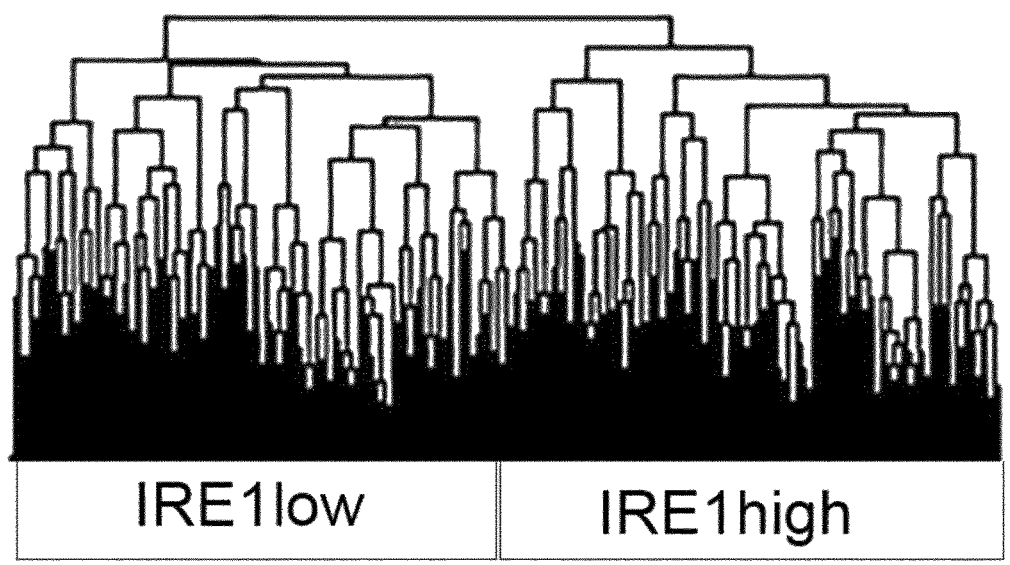

FIG. 2: IRE1 signaling signature in the GBMmark cohort. Hierarchical clustering of GBM patients (GBMmark cohort) based on high or low IRE1 activity as assessed with the expression of the IRE1 gene expression signature.

Figure 3:
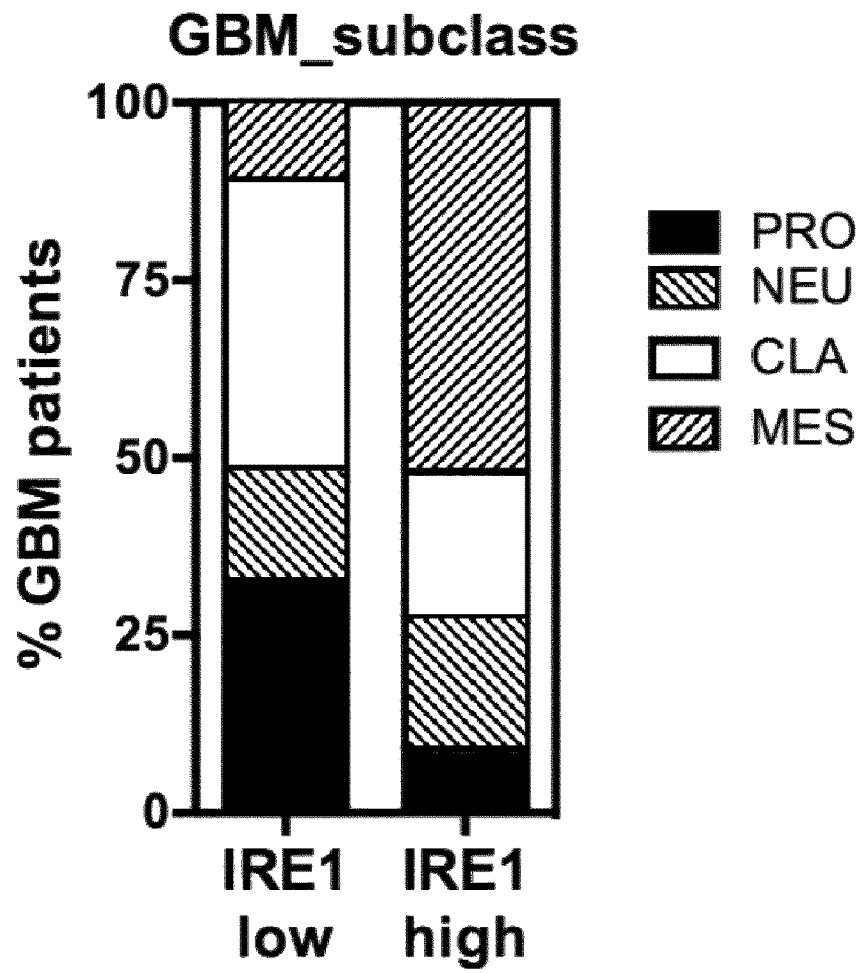

FIG. 3: IRE1 signaling signatures in GBM. Relative distribution of the different classes of GBM—proneural, neural, classic, and mesenchymal according to the tumor status, namely IRE1high or IRE1low.

FIG. 4: IRE1 signature in cancers. Evaluation of the IRE1signature in 12 cancers including glioblastoma, colon adenocarcinoma, urogenital (KIRC (kidney); OV (ovarian), melanoma, gastrointestinal (LIHC (liver); STAD (stomach); PAAD (pancreas)), BLCA (bladder)), breast cancer, lung adenocarcinoma and prostate adenocarcinoma. Tumor stratification based on IRE1sign38 was then correlated with patient survival in those cancers (as well as prostate cancer) to determine the impact IRE1 signaling characteristics have on patients' survival.

EXAMPLE

Material & Methods

Patient Samples and Primary Lines—

All tumors were frozen after surgical resection. These tumors were either clinically and genetically characterized in the department of neurosurgery of the Pellegrin Hospital (Bordeaux, France) and informed consent was obtained in accordance with the french legislation or were obtained from the processing of biological samples through the Centre de Ressources Biologiques (CRB) Sante of Rennes BB-0033-00056. The research protocol was conducted under French legal guidelines and fulfilled the requirements of the local institutional ethics committee. GBM were classified according to i) the presence of IDH1, OLIGO2 and TP53 expression and ii) tumor phenotype (size and form of tumor cells, hyperplasia, necrosis, proliferation indice). Primary GBM lines were generated as previously described. Briefly, fresh tumor tissues were mechanically dissociated using gentleMACS dissociator following the manufacturer's instructions (Miltenyi Biotec, Paris, France). RNS cells (neurospheres enriched in cancer stem cells) were directly cultured in DMEM/Ham's F12 (Lonza, Verviers, Belgium) supplemented with B27 and N2 additives (Invitrogen, Cergy Pontoise, France), EGF (20 ng/ml) and FGF2 (20 ng/ml) (Peprotech, Tebu-Bio).

IRE1 Sequencing—

IRE1 exons sequencing was performed by Beckman Coulter Genomics (Takeley, UK) using specific primers flanking exonic regions of IRE1. The presence of IRE1alpha mutation was detected using nucleotide sequence alignment software. Tumor in which IRE1 mutation was identified presented classical GBM characteristic with endothelial hyperplasia and MIB1 proliferation index of 15%, and was IDH1 negative, with 5% of OLIG2 and 5% of TP53 positive cells.

Cloning and Site-Directed Mutagenesis—

Selected punctual mutations were introduced on IRE1alpha exonic sequence using QuickChange Directed Mutagenesis kit with primers. The wild-type or mutated sequences were then cloned in the multicloning site of the expression lentivector pCDH-CMV-MCS-EF1-Puro-copGFP (System biosciences). The presence of only mutations of interest was checked by a minimum two-X cover sequencing (Beckman Coulter Genomics).

Cell Culture and Treatments—

U87MG (ATCC) and U251MG (Sigma, St Louis, Mo., USA) cells were authenticated as recommended by AACR (http://aacrjournals.org/content/cell-line-authentication-information) and tested for the absence of *mycoplasma* using MycoAlert® (Lonza, Basel, Switzerland) or MycoFluor (Invitrogen, Carlsbad, Calif., USA). U87 cells (ATCC) were grown in DMEM glutamax (Invitrogen, Carlsbad, Calif., USA) supplemented with 10% FBS. U87 were stably transfected at MOI=0.3 with pCDH-CMV-MCS-EF1-Puro-copGFP (System biosciences) empty vector (EV), pCDH-CMV-MCS-EF1-Puro-copGFP containing IRE1alpha wild-type sequence (WT) or mutated sequence (P336L, A414T, S769F or Q780*). U87 cells were selected using 2 µg/mL puromycin and polyclonal populations were tested for GFP expression. Transfections of GBM primary cell lines with IRE1 WT and Q780* were performed using Lipofectamine LTX (ThermoFisher Scientific), according to the manufacturer's instructions. For microarray experiments, tunicamycin (purchased from Calbiochem (Merck KGaA, Darmstadt, Germany)) was used at 0.5 pg/mL for 16 hrs. Actinomycin D were purchased from Sigma-Aldrich (St Louis, Mo., USA) and used as indicated. For flow cytometry, antibodies against human CD11b, CD31 and CD45 were obtained from BD Biosciences (Le Pont de Claix, France). Anti-miR-17 (miRvana) were purchased from ThermoFisher Scientific.

Semi-Quantitative PCR and Quantitative Real-Time PCR—

Total RNA was prepared using the Trizol reagent (Invitrogen, Carlsbad, Calif., USA). Semi-quantitative analyses were carried out as previously described. PCR products were separated on 4% agarose gels. All RNAs were reverse transcribed with Maxima Reverse Transcriptase (Thermo Scientific, Waltham, Mass., USA), according to manufacturer protocol. All PCR reactions were performed with a MJ Mini thermal cycler from Biorad (Hercules, Calif., USA) and qPCR with a StepOnePlus™ Real-Time PCR Systems from Applied Biosystems and the SYBR Green PCR Core reagents kit (Bio-Rad). Experiments were performed with at least triplicates for each data point. Each sample was normalized on the basis of its expression of the 18S gene.

Western Blotting and Immunofluorescence Analyses—

All IRE1 signaling analyses were carried out as described previously. Cells grown on 22-mm coverslip were washed with PBS, fixed with 4% paraformaldehyde for 10 min at room temperature, and then blocked with 5% BSA, PBS, 0.1% Triton X-100 for 1 h. ER was stained using anti-KDEL antibody (Enzo) and over expressed IRE1alpha was stained using anti-IRE1alpha antibody (SantaCruz). Cells were incubated with primary antibodies for 1 h at room temperature, washed with PBS, and incubated for 45 min with donkey anti-mouse and donkey anti-rabbit antibodies (Invitrogen). To visualize the nucleus, cells were counterstained with 1 µg/mL 4,6-diamidino-2-phenylindole (DAPI, Sigma). After mounting, cells were analyzed with a SP5 confocal microscope (Leica Microsystems, Mannheim, Germany).

Intracranial Injections, Tumor Size, and Blood Capillary Measurements—

Two independent sets of experiments were carried out using Rag-γ2 mice. Cell implantations were at 2 mm lateral to the bregma and 3 mm in depth using seven different sets of cells for U87-EV cells, U87-WT cells, U87-S769F cells, U87-Q780* cells, U87-P336L cells, U87-A414T cells and U87 IRE-DN cells. Fifteen days post injection, or at first clinical signs, mice were sacrificed, brains were frozen and sliced using a cryostat. Brain sections were stained using H&E staining or anti-vimentin antibodies (Interchim) for visualization of tumor masses. Tumor volume was then estimated by measuring the length (L) and width (W) of each tumor and was calculated using the following formula (L×W2×0.5). CD31-positive vessels were numerated after immunohistologic staining of the vascular bed using rat antibodies against CD31 (PharMingen) and fluorescent secondary antibodies (Interchim). Imaging was carried out using a Axioplan 2 epifluorescent microscope (Zeiss) equipped with a digital camera Axiocam (Zeiss). Blood vessels were quantified by two independent investigators using a blinded approach. Vessels number was measured in 12 to 20 thresholded images per condition using ImageJ software. This quantification was made three times for each image and three vessels size (surface) were reported: between 100 pixel and 500 pixels$^2$, more than 500 pixel$^2$ or more than 5000 pixel (1 pixel=0.67 µm). The average of vessel number of each size was calculated per brain. Experiments were repeated at least on five Rag-γ2 mice for each condition (up to 15). For GBM primary cell line implantation, 5×105 cells/mice were injected in immunocompromised nude mice with U87 cells. Mice were daily clinically monitored and sacrificed at the first clinical signs. Mouse brains were collected, fixed in formaldehyde solution 4% and paraffin embedded for histological analysis after H&E staining. Tumor burden was compared in the different groups of mice and analyzed using ImageJ software. Furthermore, vascularization of the tumors (CD31), macrophage infiltration (IBA1) and invasion tumor (vimentin) were monitored using immunohistochemistry.

Statistical Analyses—

Data are presented as mean±SD or SEM (as indicated). Statistical significance (p<0.05 or less) was determined using a paired or unpaired t-test or ANOVA as appropriate and performed using GraphPad Prism software (GraphPad Software, San Diego, Calif., USA).

PBMC Chemoattraction Assay—

Peripheral blood mononuclear cells (PBMC) were isolated from healthy donors. PBMC were washed in DMEM, placed in Boyden chambers (5×105 cells/chamber in DMEM) (Millipore, France) that were placed in DMEM or conditioned medium from cells treated with mirVana miRNA-17 inhibitor (ThermoFisher Scientific, Waltham, Mass., USA) and then incubated at 37° C. for 24h. The migrated PBMC (under the Boyden chambers) were collected, washed in PBS and cells were stained for monocytes, T, B and NK cell markers (anti-CD14, -CD3, -CD19 and -CD56 respectively) and analysis by flow cytometry as described below. The relative number of migrated cells was estimated by flow cytometry by counting the number of cells per minute.

Tumor Migration Assay—

Parental U251 and U87 cell lines transfected with either empty vector pcDNA 3.1/myc-His B or lenti-pCDH-IRE1 A414T, and subsequently transfected with siRNA against XBP119 or anti microRNA-17, were washed in DMEM, placed in Boyden chambers (105 cells/chamber in DMEM) that were placed in DMEM 20% FBS and incubated at 37° C. After 24 hours, Boyden chambers were washed in PBS and cells were fixed in PBS 0.5% paraformaldehyde. Non-migrated cells inside the chambers were removed and cells were then stained with Giemsa (RAL Diagnostics, Martillac, France). After washes in PBS, pictures of 5 different fields were taken. Migration was given by the mean of number of migrated cells observed per field. For GBM primary cell migration, Boyden chambers were previously coated with 0.1% collagen solution (Sigma-Aldrich).

FACS Analyses—

GBM specimens were dissociated using the gentleMACS dissociator (Miltenyi Biotec, Paris, France) according to manufacturer's recommendations and cells were directly used for flow cytometry analysis. Cells were washed in PBS 2% FBS and incubated with saturating concentrations of human immunoglobulins and fluorescent-labelled primary antibodies for 30 minutes at 4° C. Cells were then washed with PBS 2% FBS and analyzed by flow cytometry using a FACSCanto II flow cytometer (BD Biosciences). The population of interest was gating according to its FSC/SSC criteria. The dead cell population was excluded using 7-amino-actinomycin D (7AAD) staining (BD Biosciences). Data were analyzed with the FACSDiva (BD Biosciences).

Results

IRE1 Activity and Human GBM Tumor Properties

We previously identified an IRE1-dependent gene expression signature in U87 cells using IRE1 dominant negative expressing cells, an approach that fully blocks all RNAse outputs of this ER stress sensor. Functional annotation of the genes comprised in the IRE1-dependent gene expression signature revealed the enrichment in biological functions associated with stress responses, cell adhesion/migration and with the inflammatory and immune response (data not shown). This gene expression signature was processed through the Bioinfominer pipeline (FIG. 1) to increase its functional relevance and this led to the identification of 38

IRE1 signaling hub-genes (FIG. 1). This 38 genes signature was then confronted to the transcriptomes of the GBM TCGA (consortium, 2008) and GBMmark (in-house) cohorts (data not shown). This analysis revealed the existence of two populations of patients displaying either high or low IRE1 activity, respectively (FIG. 2). Tumors exhibiting high IRE1 activity also correlated with shorter survival of the corresponding patients (data not shown). We then tested the impact of IRE1 signaling on the expression levels of IBA1, CD14 and CD163 as markers of the inflammatory/immune response in the tumors (data not shown), the levels of CD31 and vWF to monitor angiogenesis (data not shown) or RHOA, CYR61 and CTGF expression as indicators of tumoral invasion (data not shown). This revealed that tumors exhibiting high IRE1 activity also presented markers of massive infiltration of macrophages, with high vascularization and invasive properties. Similar observations were also obtained when analyzing the GBMmark dataset (data not shown). Activation of the IRE1/XBP1 axis was confirmed in those tumors through the analysis of the expression of XBP1 target genes ERDJ4 and EDEM1 (data not shown). To confirm these observations at the protein level in GBM, fresh tumors presenting high or low IRE1 activity were dissociated and analyzed for CD45 and CD11b expression by FACS. This analysis revealed that high IRE1 signaling correlated with strong macrophage infiltration (data not shown). Moreover, the presence of endothelial cells in tumors was detected by FACS after CD31 labeling and was increased in GBM tumors exhibiting high IRE1 activity (data not shown). Finally, tumors exhibiting high IRE1 signaling were mainly classified as belonging to the mesenchymal type of GBM whereas those with low IRE1 activity mostly included pro-neural and classical tumors (FIG. 3). These data demonstrate that IRE1 activation is found in human tumors and correlates with more aggressive cancers with shorter patient survival.

Identification of a Novel Somatic Mutation on IRE1 in Human GBM

IRE1 activation in tumors could be due to exposure to stressful environments (nutrient/oxygen deprivation, pH, immune response) but also to the presence of somatic mutations in the IRE1 coding gene. Previous tumor sequencing studies identified IRE1 mutations that were defined as driver in various cancers among which 3 were found in GBM. Here we sequenced the IRE1 gene (ERN1) exons in twenty-three additional GBM samples and identified a fourth IRE1 mutation in one GBM human sample (data not shown). This somatic A414T mutation came from an aggressive, mesenchymal like GBM developed in a 70-year old female. Immunohistochemistry staining revealed that this tumor was also highly vascularized (CD31 staining) and showed strong XBP1s staining (data not shown). Sequence alignment indicates that whereas the mutations P336L, S769F and Q780* affect conserved amino acids in various species, the mutation identified in our sequencing study altered an apparently less conserved amino acid, which was only conserved in dog, chimpanzee and human but not in rodents (data not shown). This property could explain why the A414T mutation, previously described in GBM samples, has been excluded from further analyses, as it was considered as a SNP or a secondary acquired mutation. Interestingly since the first discovery of IRE1 somatic mutations in cancers in 2007, a number of cancer exome or whole genome sequencing studies have also reported around fifty mutations but none of them in GBM.

Different Kinase and RNAse Activities of IRE1-Related Cancer Variants

IRE1 is a bifunctional protein that contains a kinase and a RNase domain involved in three downstream signaling pathways including i) activation of stress pathways (i.e. JNK and NFKB), ii) the degradation of targeted RNAs (RIDD) and iii) the unconventional splicing of XBP1 mRNA. The localization of IRE1 mutations found in cancer revealed no apparent clustering of the mutations in the secondary structure, not even into IRE1 catalytic domains. However, the "cytosolic" mutations S769F and Q780* are located in the kinase domain of the protein whereas the "luminal" mutations P336L and A414T are located in putative alpha-helical domains (data not shown). To measure the potential impact of the four mutations found in GBM, we overexpressed either the wild type (WT) or the mutated forms of IRE1 in U87 cells, in a normal endogenous IRE1 background (data not shown). The four variants were overexpressed in U87 cells using a lentivirus system and as anticipated the stop mutation Q780* leads to overexpression of a shorter IRE1 protein (80 kDa instead of 110 kDa). Finally, immunofluorescence studies showed that IRE1 staining co-localized with an ER marker (KDEL staining) and thereby confirmed that mutations did not affect IRE1 localization to the ER (data not shown).

As reported in other cellular system, the overexpression of the WT form in U87 was sufficient to activate IRE1 in basal conditions compared to the control empty-vector (EV) expressing cells, as indicated by basal IRE1 phosphorylation, as well as XBP1 mRNA splicing (data not shown). As expected, Q780* corresponded to a loss-of-function mutation regarding the splicing of XBP1 mRNA. Indeed, the loss of the last fragment of the kinase domain and the entire RNase and C-terminus domains did not affect IRE1 oligomerization but impaired the resulting trans-autophosphorylation (data not shown) as well as XBP1 mRNA splicing (data not shown). Expression of the Q780* variant also prevented XBP1 mRNA splicing by endogenous IRE1 in response to tunicamycin treatment (data not shown). In addition, P336L and A414T mutations increased IRE1 oligomerization capacity (data not shown), leading to IRE1 hyper phosphorylation and enhanced XBP1 splicing (data not shown). It is important to note that WT-IRE1 overexpression efficiently increased RIDD activity on PERIOD1 (PER1), COL6A1 and SCARA3 mRNAs, whereas little impact was observed on other previously reported RIDD substrates such as SPARC, PDGFRbeta and VEGFA mRNAs, thereby pointing towards RIDD selectivity associated with IRE1 variants. As such the four mutations had different effects depending on the targeted mRNA (data not shown). This substrate selectivity might result from modifications in IRE1 binding to luminal or cytosolic partners due to IRE1 over expression or mutations (i.e. altered oligomerization or signaling properties). Finally, following the observation of Upton and colleagues, we found that IRE1 variants RNase activity controlled miR-17 (miR-17-5p) expression in GBM. Indeed, the A414T variant led to increased miR-17 expression under basal conditions while the P336L variant led to low miR-17 levels (data not shown). IRE1 RNase inhibition mediated by MKC4485 restored the expression of miR-17 in P336L IRE1 variant expressing U87 cells (data not shown), thus confirming the involvement of IRE1 RNase in miR-17 expression. Tunicamycin-induced ER stress engaged IRE1 activation and led to further miR-17 degradation (data not shown).

U87 Phenotype and Signaling Upon Expression of IRE1 Variants

To further investigate the impact of IRE1 variants expression in U87 cells, we first evaluated the cellular phenotypes generated using phase microscope imaging. All the cells presented a mesenchymal phenotype comparable to U87 transfected with an empty vector (data not shown) or parental U87 (not shown), except for those expressing the IRE1 P336L variant, which displayed an epithelial-like phenotype. These cells exhibited similar proliferation rates (data not shown) and still had the capacity of forming spheres in culture (data not shown) as described previously. To further evaluate the IRE1-dependent signaling aspects in GBM, we used the KEGG pathway for glioma that compiles the main actors involved in gliomagenesis, and identified the components that were previously shown to be directly or indirectly regulated by IRE1. This revealed that 45% of the components comprised in this pathway were controlled through IRE1-dependent mechanisms (data not shown). We then monitored the expression levels of PDGFRbeta and p53 (data not shown). PDGFRbeta expression was highly expressed in cells expressing EV and the P336L mutant. Interestingly, the expression of wild type p53 in U87 cells was upregulated by 15-fold in P336L expressing cells. In those cells, p53 mRNA was not altered compared to EV cells (data not shown) and no mutations were found by sequencing (not shown), thereby suggesting a translational regulation of the protein. To further characterize the impact of the IRE1 variants on cell signaling pathways we used a transcriptomic approach. Hierarchical clustering revealed that WT IRE1 grossly behaved as the S769F, Q780* and P336L variants under basal and stress conditions. In contrast, cells expressing the IRE1 A414T variant exhibited a very different gene expression profile than the other cell types that more closely resembled the signature observed in IRE1-DN cells. The expression profiles were then analyzed for signaling pathway activation and unveiled possible pathways selectively activated by IRE1-related cancer variants (data not shown). Functional analysis of the gene enrichment pattern indicated a major impact of IRE1 A41AT mutation on signaling pathways involved in metabolism control, extracellular matrix (ECM) organization and cell homeostasis maintenance, whereas IRE-DN impacted mostly genes related to ECM organization, cell homeostasis and the immune system. Interestingly, the impact of other variants on basic cellular signaling functions remained limited compared to the pattern elicited by IRE1 A414T and DN expression (data not shown).

Modulation of Tumor Development In Vivo Upon Expression of IRE1 Variants

To evaluate the significance of each IRE1 variant to tumor growth in vivo, we implanted control U87 or cells expressing WT and mutated forms of IRE1 into mouse brain. Fifteen days post-implantation, five animals of each group were scarified and brains isolated for immunofluorescence (IF) staining of tumor cells (vimentin) and vessels (CD31). As expected, IRE1 overexpression impacted tumor growth and vascularization, whereas impairment of IRE1 signaling (IRE1-DN) reduced both size and vascularization of the tumors (data not shown). An exception of this tumorigenic effect of IRE1 was observed with the P336L mutation. Indeed, injection of U87 expressing the IRE1 P336L never led to the formation of a visible tumor (>15 injections). This phenomenon may be a consequence of the observed overexpression of the tumor suppressor p53 in those cells (data not shown), leading to the attenuation of U87 aggressive phenotype.

Among the four mutations, the loss-of-function mutations S769F and Q780* appeared to have little effects on mouse survival (data not shown), however, the Q780* mutation accelerated the early steps of tumor growth compared to the control tumors (data not shown). Remarkably, expression of the P336L and A414T variants, which exhibited similar gain-of-function on IRE1 in vitro, showed diametrically opposed behaviors in vivo on tumor development. Indeed, whereas P336L totally blocked tumor formation, A414T shortened mouse survival (data not shown), most likely by promoting tumor growth and vascularization with hallmarks of vessel cooption (data not shown). Interestingly, tumors formed from EV, WT and A414T cells showed high XBP1s expression as assessed by immunohistochemistry which did not account for the differences observed in mouse survival (data not shown). Remarkably, the pro-angiogenic effects of the A414T mutation not only increased the number of vessels associated with the tumor mass, but also increased the size of those vessels (data not shown), an effect that was much less visible in early steps of tumorigenesis (data not shown). Furthermore, the impact of the A414T mutation on the immune infiltrate to the tumor site was also evaluated in vivo and showed that expression of this IRE1 variant in U87 cells resulted in the formation of tumors presenting very low levels of macrophage infiltration (data not shown). This was not the case for other variants (data not shown). Finally, tumor-infiltrating spots were quantified as previously described and showed major infiltration/invasion of DN as previously observed but also a significant positive impact of the expression of the A414T variant (data not shown). Thus, our results suggest that selective genetic alterations affecting IRE1 activity condition the specific biological outputs observed at the level of tumor growth, survival, angiogenesis and immune cell infiltration.

IRE1 Downstream Signals Drive Changes in the Tumor Microenvironment

To further dissect the contribution of signals downstream of IRE1 in GBM tumor phenotypes, we took advantage of the properties of IRE1 variants. Global analysis of our results highlights the signaling differences driven by IRE1 mutant forms where WT IRE1, the P336L, and A414T variants exhibited high XBP1 mRNA splicing and RIDD activities whereas the expression of miR-17 was elevated in cells expressing WT or IRE1-DN as well as those expressing the A414T variant (data not shown). Based on this analysis we reasoned that genes whose expression were upregulated in WT, P336L and A414T could reflect targets under the control of XBP1s. Using the transcriptome profiles, we identified a list of 40 genes that segregate with high XBP1s levels (data not shown). We then used the XBP1s signature to classify tumors from the GBMmark cohort (data not shown) and analyzed the expression of IBA1, CD31 and RHOA in tumors exhibiting high or low expression of XBP1s target genes (data not shown). This revealed that the three markers studied showed higher expression levels in tumors with high XBP1s target gene expression. This was further confirmed using immunohistochemistry with antibodies against XBPs and IBA1. A total of thirty-five cases of GBM were analyzed with anti-XBP1s and revealed either no staining (data not shown) or staining in the nucleus (data not shown) and in the cytoplasm (data not shown). A subset of those tumors (n=24) was then analyzed for IBA1 expression (data not shown) and a correlation between the presence of IBA1 and that of XBP1s was established thereby indicating that high XBP1s in the tumor may control immune cell (macrophage) infiltration (data not shown).

Next, we investigated how RIDD activity could impact on tumor characteristics. To this end, we determined a potential RIDD signature based on the ability of IRE1 to cleave select mRNA in vitro. This screening identified a group of 1141 mRNAs susceptible to be cleaved in vitro by IRE1 (data not shown), which were then intersected with the set of genes up-regulated in IRE1-DN cells. This analysis yielded a subset of 37 potential GBM-specific RIDD targets (data not shown). Their functional annotation suggests the enrichment in genes involved in the NOD pathway, interaction with the environment and biogenesis of cellular components (data not shown). Then, this cluster of mRNAs was used to identify RIDD-positive and -negative tumor populations in the GBMmark cohort (data not shown). The expression of immune infiltration, angiogenesis and invasion markers in these populations confirmed previous results and ruled out tumoral RIDD of mRNA in the recruitment of immune cells (data not shown). In summary, in contrast to the IRE1/XBP1 axis that exhibits pro-tumorigenic signaling features, the RIDD of mRNA pathway may antagonize tumor invasion and angiogenesis with no significant effect on immune cells infiltration.

Differential Contribution of RIDD and XBP1 mRNA Splicing to GBM

We then investigated the role of IRE1/miR-17 axis in cancer progression. To this end we took advantage of the properties of the different IRE1 variants towards miR-17 (data not shown) and established a minimal group of genes whose expression could be under the control of miR-17 (data not shown). This set of genes is involved in morphogenetic programs, cell adhesion, synthesis of aromatic compounds and to a lesser extend in the response to reactive oxygen species (data not shown). This information was then used to evaluate tumors with high or low IRE1/miR-17 in the GBMmark cohort and to monitor the expression of IBA1, CD14, CD31, vWF, RHOA and CTGF (data not shown). As for RIDD of mRNA, these data indicated that RIDD for miR-17 exhibited anti-angiogenic and anti-migratory effects. This led us to correlate high RIDD IRE1 activity, which might lead to low miR-17 expression, and better outcome in GBM patients. To test this hypothesis, we evaluated the expression of miR-17-5p in 30 GBM tumors and identified two groups of tumors exhibiting low or high miR-17-5p expression (data not shown). Patient survival was evaluated in those two groups of patients and revealed that low miR-17-5p levels in tumors correlate with better survival than those patients presenting high miR-17-5p tumors (data not shown), thereby confirming our initial hypothesis. To functionally explore the role of the IRE1/miR-17 axis in GBM development, we blunted miR-17 activity with anti-miR-17 sponges in EV and A414T cells and tested the expression of predicted miR-17 target genes. We confirmed that antagonizing miR-17 increases the expression of miR-17 targets in cells expressing the A414T IRE1 variant (data not shown). To further evaluate the functional role of miR-17 in GBM, we monitored the impact of either XBP1 silencing or antagonizing miR-17 in U87 or U251 cells expressing an empty vector or the IRE1 A414T variant. This approach revealed that siRNA-mediated XBP1 silencing in U87 cells impaired monocyte chemo-attraction (data not shown) whereas antagonizing miR-17 did not have any significant effect (not shown). In addition, we found that overexpression of IRE1 A414T in U251 cells increased cell migration using a trans-well assay, a feature that was impaired by XBP1 silencing or miR-17 buffering (data not shown).

Our data led us to propose a complex model in which the IRE1/XBP1 signaling axis would promote GBM aggressiveness through the enhancement of tumor immune infiltration and angiogenesis as well as tumor cell invasiveness properties, whereas RIDD (of mRNA and miRNA) would play an anti-tumoral role by selectively reducing tumor angiogenesis as well as tumor cell invasiveness (data not shown). To further demonstrate the divergent activities of IRE1 in cancer, the TCGA cohorts (microarrays and RNAseq) were analyzed for populations exhibiting low and high XBP1 splicing and RIDD activities. Hierarchical clustering revealed four major groups as follows XBP1s$^{high}$/RIDD$^{low}$ (XBP1+/RIDD−); XBP1s$^{low}$/RIDD$^{low}$ (XBP1−/RIDD−); XBPXs$^{low}$/RIDD$^{high}$ (XBP1−/RIDD+) and XBP1s$^{high}$/RIDD$^{high}$ (XBP1+/RIDD+) (data not shown). Remarkably, patient survival analysis in the XBP−/RIDD+ and XBP+/RIDD− populations revealed that a clear segregation where the former group survived statistically longer than the latter as suggested from our working model (data not shown). Moreover, as anticipated, XBP1+/RIDD− GBM exhibited higher expression IBA1, CD31 and RHOA than the XBP1−/RIDD+ tumors (data not shown). This was also confirmed by the fact that the XBP1+/RIDD− population was enriched in mesenchymal tumors whereas XBP−/RIDD+ comprised more pro-neural and neural tumors (data not shown). Interestingly, when the splicing of XBP1 was evaluated in the TCGA RNAseq cohort and compared to the XBP1+ groups established using our method, we correlated both information thereby confirming the validity of our approach (data not shown). Finally, differences in the survival of the patients belonging to the intermediate groups (i.e. XBP1−/RIDD−; XBP1+/RIDD+) were not statistically significant (data not shown). Taken together, these experiments suggest a combined/integrated role of XBP1 mRNA splicing and RIDD in GBM specifically regarding cell migration and angiogenesis.

Modeling IRE1 Contribution to GBM Development in Primary GBM Lines

We then tested whether the tumor classification was also relevant in primary GBM lines, that could in turn serve as an in vitro model for better understanding the role of IRE1 signaling in GBM development. We therefore applied the same clustering method on the transcriptome datasets from 12 primary GBM lines. This revealed that the 12 lines clustered into the same 4 groups as observed for the tumors (data not shown). These tumor lines exhibited various phenotypes in culture, notably regarding adhesion/protrusion/migration (data not shown). Interestingly high adhesion/migration also correlated with the XBP1+ status. This was confirmed using RT-qPCR with lines belonging to the XBP1+ group exhibiting the highest XBP1s levels (data not shown). This information however was not further correlated with the in vitro migration properties of the primary lines (data not shown). To further evaluate the relevance of the classification, the 12 lines were orthotopically injected in mice and the resulting tumors evaluated using vimentin staining (data not shown). Together with the tumor size (data not shown) and the survival data (data not shown), these experiments confirmed that XBP1+/RIDD− tumor cells yielded the most aggressive tumors whereas injecting XBP1−/RIDD+ tumor cells resulted in very small tumors, thereby confirming the results observed in patients' tumors (data not shown). We then monitored both macrophage recruitment to the tumors as well as angiogenesis and showed that although high XBP1s correlated with important macrophage infiltration in the tumors (data not shown), tumoral large vessels content did not significantly change in the different groups (data not shown). Interestingly, the expression levels of CCL2 correlated with high XBP1s (data not shown) whereas that of VEGF did not (data not shown). These data show that primary GBM lines recapitulate, at least partially, the IRE1 signaling properties observed in human tumors and maintain the expected biological outputs even in vivo.

We then further tested whether altering IRE1 activity in those cells could impact on their tumoral properties. To this end, we overexpressed IRE1 WT and the Q780* mutant (known to impair XBP1s (data not shown) in four primary lines, namely RNS85, RNS87, RNS96 and RNS130. The lines were selected on the basis of IRE1 mRNA expression (data not shown) and then analyzed by Western blot with anti IRE1 antibodies (data not shown). As expected, IRE1 expression was higher upon overexpression on IRE1 WT and the shorter form of IRE1 observed upon expression of the Q780* variant. These different lines were then monitored for the splicing of XBP1 mRNA (data not shown) and for the expression of UPR target genes (data not shown). Again, these analyses confirmed that in RNS85, 87, 96 and 130, overexpression of IRE1 increased IRE1 activity, thereby resulting in an increased expression of select target genes whereas the expression of the Q780* variant resulted in blunting XBP1s signaling. To further investigate the role of IRE1 modulation in those lines, we first tested how IRE1 activation or inhibition affected the expression of genes related to cell migration (EMT) and chemokine production. This revealed that overexpression of WT IRE1 increased the expression of the EMT-related genes VIM, ZEB1 and TGFB2 whereas that of Q780* IRE1 did not affect it when compared to the control parental line (data not shown). Similar results were also observed for the expression of the chemokines CXCL2, CCL2 and IL6 (data not shown), thereby confirming the contribution of IRE1 signaling to those pathways.

We then monitored the functional effects of IRE1 modulation in primary lines on tumor cell migration since the cellular phenotypes were altered when expressing IRE1 WT or mutant (data not shown). This was carried out using Boyden chambers-based assays (data not shown) and quantitation showed that in most cases IRE1 activation promoted cell migration whereas IRE1 inhibition completely abrogated it in all primary lines tested (data not shown). As we previously showed that IRE1/XBP1 signaling was also involved in monocytes chemoattraction, we tested whether modulating IRE1 activity in primary lines would affect this property using Boyden chamber-based migration and FACS analyses (data not shown). Quantitation of the results showed that, as observed for migration, enhancing IRE1 activity led to increased chemoattraction whereas blunting XBP1s through the expression of IRE1 Q780* resulted in decreased capacity to attract monocytes in the four primary lines tested (data not shown). These results obtained in primary GBM lines confirm our previous observations in U87 cells and in human tumor samples and support our model in which IRE1 activity could control the specific properties of GBM tumor cells through the combined action of XBP1s and RIDD.

Evaluation of IRE1signature in Various Cancers

We evaluated the IRE1 signature in 12 cancers and we analyzed the patient's survival in those cancers (FIG. 4).

Discussion

Our work demonstrates that in GBM IRE1 downstream signals, including XBP1 mRNA splicing and RIDD, dictate tumor phenotypes and patient outcomes. At first, we showed the relevance of IRE1 signaling in GBM from two independent cohorts (TCGA and GBMmark) and found that high IRE1 activity correlates with shorter patient survival and increased tumor infiltration by immune cells, increased tumor angiogenesis and enhanced invasion/migration properties of the tumor cells. Previous studies demonstrated the importance of IRE1 signaling for tumor aggressiveness, however they did not provide any information on the underlying molecular mechanisms involved in this phenomenon. Previous studies established the IRE1 molecular signature using various exogenous acute stresses, such as hypoxia and nutrient deprivation. However, the use of such micro-environmental challenges did not recapitulate the complexity of brain cancer as an experimental mean to define the molecular mechanisms downstream of IRE1 involved in tumor growth. Thus, we reasoned that mutations identified on IRE1 in GBM could serve as interesting tools to characterize how specific IRE1-dependent signaling pathways could control tumor phenotypes at both the tumor cell and stroma levels. IRE1 mutations in GBM were previously reported but the functional consequences of those mutations on IRE1 signaling remained undocumented. To further expand the repertoire of IRE1 mutations in GBM we sequenced the IRE1 gene in 23 additional GBM tumors, and then analyzed the signaling characteristics of the variants identified.

In the present study, we have characterized in detail IRE1 somatic variants using complementary approaches and uncovered a novel mutation in IRE1 on the A414 residue. Expression of this variant in U87 cells led to highly aggressive cancer with enhanced vascularization and reduced infiltration of macrophages to the orthotopic tumors. This result was difficult to explain only on the basis of the signaling characteristics of this mutant and suggested a highly complex integrated IRE1 signal accounting for both XBP1 mRNA splicing and RIDD characteristics to produce the observed tumor phenotype. This was reinforced by our work on the P336L mutation which is, so far, the only IRE1 mutation identified in more than one tumor sample and even in more than one cancer type (one in glioma and two in intestinal cancers), thereby confirming its relationship to cancer development. We thus hypothesized that the oncogenic potential of this mutation may need a particular cancer context, such as the presence of acquired mutation in key genes for GBM development (EGFR, PTEN, TP53, NF1 and IDH1), as no previous study defined P336L as a driver mutation. We showed that TP53 was overexpressed in IRE1-P336L expressing U87 cells which most likely promoted tumor suppression in vivo (TP53 wild type in U87). This observation rules out the driver role of this mutation that would only subsist in a P53 mutant background. Moreover, recent work reported a direct role of the IRE1 target JNK in stabilizing EGFR ligand epiregulin (EREG) and consequently an autocrine activation loop of EGFR, which should provide proliferative advantage of GBM cells in which EGFR signaling was already altered by mutations. This hypothesis could also explain the proliferative effects of A414T mutation and future studies should define the involvement of EGFR or other key GBM proteins in IRE1 dependent GBM growth, as both P336L and A414T mutations seemed to stabilize IRE1 kinase and RNases activities. Hence, the signaling characteristics of IRE1 variants confer GBM tumors with specificities that could lead to aggressive features.

We took advantage of the signaling characteristics of IRE1 variants associated with GBM and the fact that we characterized the transcriptome of U87 cells expressing those variants under basal and ER stress conditions to delineate specific molecular signatures of each distinct IRE1 signaling output. This analysis revealed that the XBP1s signaling axis promoted tumor infiltration by immune cells, increased angiogenesis and enhanced the expression of migration/invasion markers. Interestingly, these properties were also confirmed using approaches relying on immunohistochemical analyses on a different subset of tumors. In contrast, RIDD activity (toward either mRNA or miR-17) attenuated both the angiogenic response and the migration/invasion properties of the tumor cells. The opposite signals elicited by XBP1s and RIDD confer specific aggressive features to tumors with XBP+/RIDD− tumors associated with a worse prognostic outcome than those with XBP−/RIDD+ properties. Interestingly, tumors with low RIDD/XBP1s and those with high XBP1s/RIDD did not yield different prognoses in terms of patient survival most likely due either to the major contribution of other pathways still to be identified (i.e. EGFR, P53) or to compensatory mechanisms of both pathways, respectively. Beyond the characterization of these signaling properties in U87 cells and in human tumors, we also demonstrated that those pathways were also conserved in primary GBM lines and that their modulation had a significant impact on the tumor cells phenotypes. These pathology-relevant tools will now be useful to define how IRE1 signals towards XBP1s or RIDD are regulated at the level of IRE1 and how those two signaling arms quantitatively interact to drive specific tumor characteristics. Moreover, RIDD of miRNA (miRIDD) activity could interact with known pro-tumoral pathways in GBM through regulation of other IRE1 miRNA targets such as miR-34a.

In addition to providing the first evidence of the co-existence of combined/integrated IRE1 downstream signals in GBM and correlating those with tumor aggressiveness features, our work highlights the possibility of using IRE1-targeted therapeutics in cancer. Indeed, it is likely that in XBP1+/RIDD− tumors, inhibition of IRE1 RNase with small molecules or selective inhibition of the XBP1 mRNA ligase RtcB might lead to significant impairment of tumor growth. This type of strategy would be highly relevant for tumor cells exhibiting constitutive expression of XBP1s such as triple negative breast cancers. Similarly, an approach aiming at increasing RIDD activity in XBP1-/RIDD+ tumors to induce cell death mechanisms would be predicted to sensitize GBM cells to chemotherapies such as TMZ. This could for instance be achieved by using inhibitors of BiP that were successfully tested in melanoma. In addition to the direct effect of IRE1 inhibitors on the tumor cells, one might also consider their use in combination with current therapies, the most common of which comprising the combination of radio- and chemotherapy (the latter with the alkylating agent TMZ). Provided that about half of GBM patients are resistant to TMZ, their stratification in terms of TMZ sensitization through selective IRE1 inhibition would represent an appealing therapeutic alternative.

Collectively, our work demonstrates for the first time that the uncoupling of XBP1s and RIDD signals downstream of IRE1 impacts on cancer development and points towards an alternative therapeutic avenue coupled with personalized molecular diagnosis for i) decreasing tumor cells adaptive properties, ii) enhancing RNA catabolic pathways leading to accelerated tumor cell death and iii) modulating the tumor stroma through reduced angiogenesis and increased anti-tumor immunity. These approaches combined with a better knowledge of GBM IRE1 signaling characteristics may contribute to develop a new precision medicine tool for GBM treatment.

REFERENCES

Throughout this application, various references describe the state of the art to which this invention pertains. The disclosures of these references are hereby incorporated by reference into the present disclosure.

The invention claimed is:

1. A method for predicting whether a human subject will be eligible for treatment with an IRE1 RNase inhibitor and treating said subject comprising:
   i) determining an expression level of ASS1, C3, CCL20, COL4A6, CXCL2, CXCL5, CXCL8, IFI44L, IL1B, IL6, KCNN2, MMP1, MMP12, MMP3, PLA2G4A, PPP4R4, SERPINB2, TFPI2, ZNF804A, ANGPT1, CFH, CFI, CLEC3B, COL3A1, COL8A1, DACH1, DCN, FHL1, GAS1, LUM, OXTR, PLAC8, RGS4, TAGLN, TGFB2, THBS1, TIMP3 and/or TMEM255A in a tumor sample obtained from the subject,
   ii) comparing the expression level of each gene determined at step i) with its respective predetermined reference level,
   iii) concluding that the subject is eligible for treatment with an inhibitor of IRE1 RNase when the expression level determined at step i) for ASS1, C3, CCL20, COL4A6, CXCL2, CXCL5, CXCL8, IFI44L, IL1B, IL6, KCNN2, MMP1, MMP12, MMP3, PLA2G4A, PPP4R4, SERPINB2, TFPI2 and/or ZNF804A is lower than the respective predetermined reference level and the level determined at step i) for ANGPT1, CFH, CFI, CLEC3B, COL3A1, COL8A1, DACH1, DCN, FHL1, GAS1, LUM, OXTR, PLAC8, RGS4, TAGLN, TGFB2, THBS1, TIMP3 and/or TMEM255A is higher than its predetermined reference level,
   or concluding that the subject is eligible for treatment with an inhibitor of IRE1 RNase when the expression level determined at step i) for ASS1, C3, CCL20, COL4A6, CXCL2, CXCL5, CXCL8, IFI44L, IL1B, IL6, KCNN2, MMP1, MMP12, MMP3, PLA2G4A, PPP4R4, SERPINB2, TFPI2 and/or ZNF804A is higher than the respective predetermined reference level and the level determined at step i) for ANGPT1, CFH, CFI, CLEC3B, COL3A1, COL8A1, DACH1, DCN, FHL1, GAS1, LUM, OXTR, PLAC8, RGS4, TAGLN, TGFB2, THBS1, TIMP3 and/or TMEM255A is lower than its predetermined reference level, and
   iv) administering to the subject a therapeutically effective amount of an IRE1 RNase inhibitor when the subject is eligible for treatment with an IRE1 RNase inhibitor.

2. The method of claim 1, wherein the subject suffers from cancer.

3. The method of claim 1, wherein the subject suffers from neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis *coli*; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; non encapsulating sclerosing carcinoma; adrenal cortical carcinoma; endometroid carcinoma; skin appendage carcinoma; apocrine adenocarcinoma; sebaceous adenocarcinoma; ceruminous; adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; Sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malign melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brennertumor, malignant; phyllodestumor, malignant; synovial sarcoma; mesothelioma, malignant; dysgerminoma; embryonal carcinoma; teratoma, malignant; strumaovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblasticodontosarcoma; ameloblastoma, malignant; ameloblasticfibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocyticleukemia; mast cell leukemia; megakaryoblasticleukemia; myeloid sarcoma; or hairy cell leukemia.

4. The method of claim 1, wherein the subject suffers from bile duct cancer, bladder cancer, bone cancer, brain and central nervous system cancer, breast cancer, Castleman disease, cervical cancer, colorectal cancer, endometrial cancer, esophagus cancer, gallbladder cancer, gastrointestinal carcinoid tumors, Hodgkin's disease, non-Hodgkin's lymphoma, Kaposi's sarcoma, kidney cancer, laryngeal and hypopharyngeal cancer, liver cancer, lung cancer, mesothelioma, plasmacytoma, nasal cavity and paranasal sinus cancer, nasopharyngeal cancer, neuroblastoma, oral cavity and oropharyngeal cancer, ovarian cancer, pancreatic cancer, penile cancer, pituitary cancer, prostate cancer, retinoblastoma, rhabdomyosarcoma, salivary gland cancer, skin cancer, stomach cancer, testicular cancer, thymus cancer, thyroid cancer, vaginal cancer, vulvar cancer, or uterine cancer.

5. The method of claim 1, wherein the subject suffers from glioblastoma, melanoma or colorectal cancer.

* * * * *